US012606753B2

(12) United States Patent
Li et al.

(10) Patent No.: US 12,606,753 B2
(45) Date of Patent: Apr. 21, 2026

(54) RADIAL FLOW MOVING BED REACTOR FOR CATALYTIC CRACKING OF LIGHT HYDROCARBONS

(71) Applicant: Chevron U.S.A. Inc., San Ramon, CA (US)

(72) Inventors: Lin Li, San Ramon, CA (US); Huping Luo, Moraga, CA (US); Xiaoying Ouyang, El Cerrito, CA (US); Alexander E. Kuperman, Midland, MI (US); Steven Xuqi Song, Albany, CA (US); Christopher Declan Lane, Kensington, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 245 days.

(21) Appl. No.: 18/500,668

(22) Filed: Nov. 2, 2023

(65) Prior Publication Data

US 2025/0145894 A1     May 8, 2025

(51) Int. Cl.
| | |
|---|---|
| *C10G 50/00* | (2006.01) |
| *C07C 2/76* | (2006.01) |
| *C10G 11/16* | (2006.01) |

(52) U.S. Cl.
CPC ............... *C10G 50/00* (2013.01); *C07C 2/76* (2013.01); *C10G 11/16* (2013.01);
(Continued)

(58) Field of Classification Search
CPC ........... C10G 50/00; C10G 11/16; C07C 2/76
See application file for complete search history.

(56) References Cited

U.S. PATENT DOCUMENTS

| | | | |
|---|---|---|---|
| 2013/0158324 A1 | 6/2013 | Waycuilis et al. | |
| 2018/0229198 A1 | 8/2018 | Behkish et al. | |

(Continued)

FOREIGN PATENT DOCUMENTS

| | | | | |
|---|---|---|---|---|
| CN | 100567460 C | 12/2009 | | |
| EP | 0205598 B1 | 1/1992 | | |
| WO | WO-2012078506 A2 * | 6/2012 | ............... | C07C 2/76 |

OTHER PUBLICATIONS

PCT/US2024/042135, International Search Report, Nov. 28, 2024, 6 pages.

*Primary Examiner* — Renee Robinson
(74) *Attorney, Agent, or Firm* — Michael E. Carmen; Terrence M. Flaherty

(57) ABSTRACT

A process includes flowing a catalyst composition comprising catalyst particles into a radial flow moving bed reactor, wherein the catalyst particles move by gravity through the radial flow moving bed reactor to an exit point of the radial flow moving bed reactor, wherein the catalyst particles form a moving catalyst bed in the radial flow moving bed reactor, flowing a light hydrocarbon feed stream comprising $C_1$ to $C_3$ alkanes into the radial flow moving bed reactor in a manner so that the light hydrocarbon feed stream flows radially inward or radially outward through the moving catalyst bed and thereby contacts the catalyst particles under reaction conditions to produce a product effluent stream comprising a $C_2$ to $C_{10}$ hydrocarbon product and hydrogen, and flowing the product effluent stream from the radial flow moving bed reactor.

10 Claims, 10 Drawing Sheets

(52) U.S. Cl.
CPC ................ *C10G 2300/1025* (2013.01); *C10G 2300/4006* (2013.01); *C10G 2300/4012* (2013.01)

(56)                    References Cited

U.S. PATENT DOCUMENTS

2020/0157435 A1      5/2020   Alarifi et al.
2021/0309921 A1 *  10/2021   Alarifi .................... C10G 11/16
2021/0336261 A1 *  10/2021   Zhang ..................... B01J 8/087

* cited by examiner

RADIAL FLOW MOVING BED REACTOR FOR CATALYTIC CRACKING OF LIGHT HYDROCARBONS

BACKGROUND

The ongoing search for alternatives to crude is increasingly driven by a number of factors. These include diminishing petroleum reserves, higher anticipated energy demands, and heightened concerns over greenhouse gas emissions from sources of non-renewable carbon. In view of its abundance in natural gas reserves, as well as in gas streams obtained from biological sources (biogas), natural gas has become the focus of a number of possible routes for providing liquid hydrocarbons. Natural gas occurs underground and is present as a gas when it comes out of the ground. Natural gas primarily consists of methane ($CH_4$), and additionally some flammable compounds such as ethane ($C_2H_6$) and propane ($C_3H_8$). Accordingly, converting light hydrocarbons such as methane to high value products such as hydrogen, olefins and aromatics has become an attractive option.

SUMMARY

In accordance with an illustrative embodiment, a process comprises:

flowing a catalyst composition comprising catalyst particles into a radial flow moving bed reactor, wherein the catalyst particles move by gravity through the radial flow moving bed reactor to an exit point of the radial flow moving bed reactor, wherein the catalyst particles form a moving catalyst bed in the radial flow moving bed reactor, flowing a light hydrocarbon feed stream comprising $C_1$ to $C_3$ alkanes into the radial flow moving bed reactor in a manner so that the light hydrocarbon feed stream flows radially inward or radially outward through the moving catalyst bed and thereby contacts the catalyst particles under reaction conditions to produce a product effluent stream comprising a $C_2$ to $C_{10}$ hydrocarbon product and hydrogen, and flowing the product effluent stream from the radial flow moving bed reactor.

In accordance with another illustrative embodiment, a process comprises:

processing a light hydrocarbon feed stream comprising $C_1$ to $C_3$ alkanes in a series of radial flow moving bed reactors, wherein processing in a first radial flow moving bed reactor in the series of radial flow moving bed reactors comprises:

flowing a first catalyst composition comprising catalyst particles into a first radial flow moving bed reactor, wherein the catalyst particles move by gravity through the first radial flow moving bed reactor to an exit point of the first radial flow moving bed reactor, wherein the catalyst particles form a moving catalyst bed in the first radial flow moving bed reactor, flowing the light hydrocarbon feed stream comprising $C_1$ to $C_3$ alkanes into the first radial flow moving bed reactor in a manner so that the light hydrocarbon feed stream flows radially inward or radially outward through the moving catalyst bed and thereby contacts the catalyst particles under reaction conditions to produce a product effluent stream comprising a $C_2$ to $C_{10}$ hydrocarbon product, hydrogen and unreacted $C_1$ to $C_3$ alkanes, flowing the product effluent stream into a second radial flow moving bed reactor for further processing, flowing spent catalyst from the series of radial flow moving bed reactors to a catalyst regeneration unit, regenerating the spent catalyst in the catalyst regeneration unit, and flowing the regenerated catalyst from the catalyst regeneration unit to the series of radial flow moving bed reactors.

BRIEF DESCRIPTION OF THE DRAWINGS

In combination with the accompanying drawings and with reference to the following detailed description, the features, advantages, and other aspects of the implementations of the present disclosure will become more apparent, and several implementations of the present disclosure are illustrated herein by way of example but not limitation. The principles illustrated in the example embodiments of the drawings can be applied to alternate processes and apparatus. Additionally, the elements and features shown in the drawings are not necessarily to scale, emphasis instead being placed upon clearly illustrating the principles of the example embodiments. Certain dimensions or positions may be exaggerated to help visually convey such principles. In the drawings, the same reference numerals used in different embodiments designate like or corresponding, but not necessarily identical, elements. In the accompanying drawings.

3 a light hydrocarbon feed comprising $C_1$-$C_3$ alkanes to a product effluent stream comprising a $C_2$ to $C_{10}$ hydrocarbon product and hydrogen, according to another illustrative embodiment.

Figure 5A:
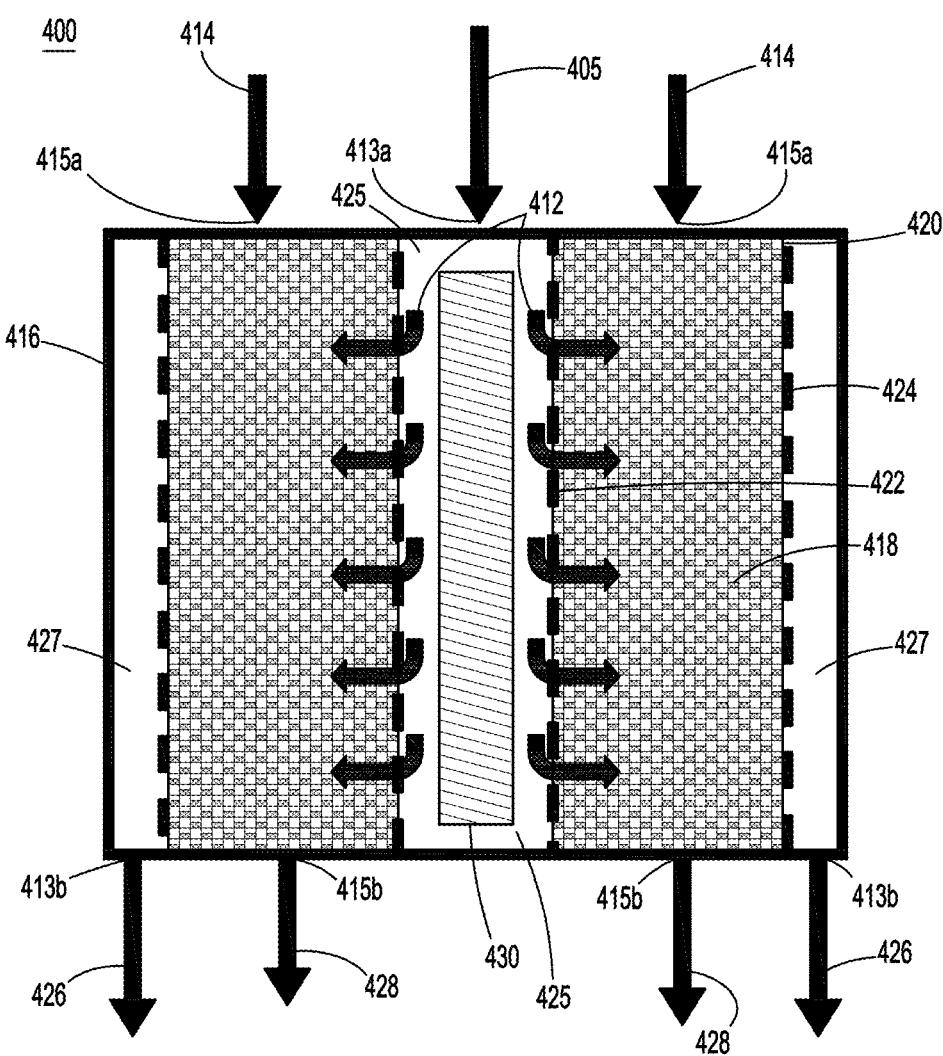
FIG. 5A illustrates a system with a radial flow moving bed reactor with an internal heating element for use in converting a light hydrocarbon feed comprising $C_1$-$C_3$ alkanes to a product effluent stream comprising a $C_2$ to $C_{10}$ hydrocarbon product and hydrogen, according to an illustrative embodiment.
Figure 5B:
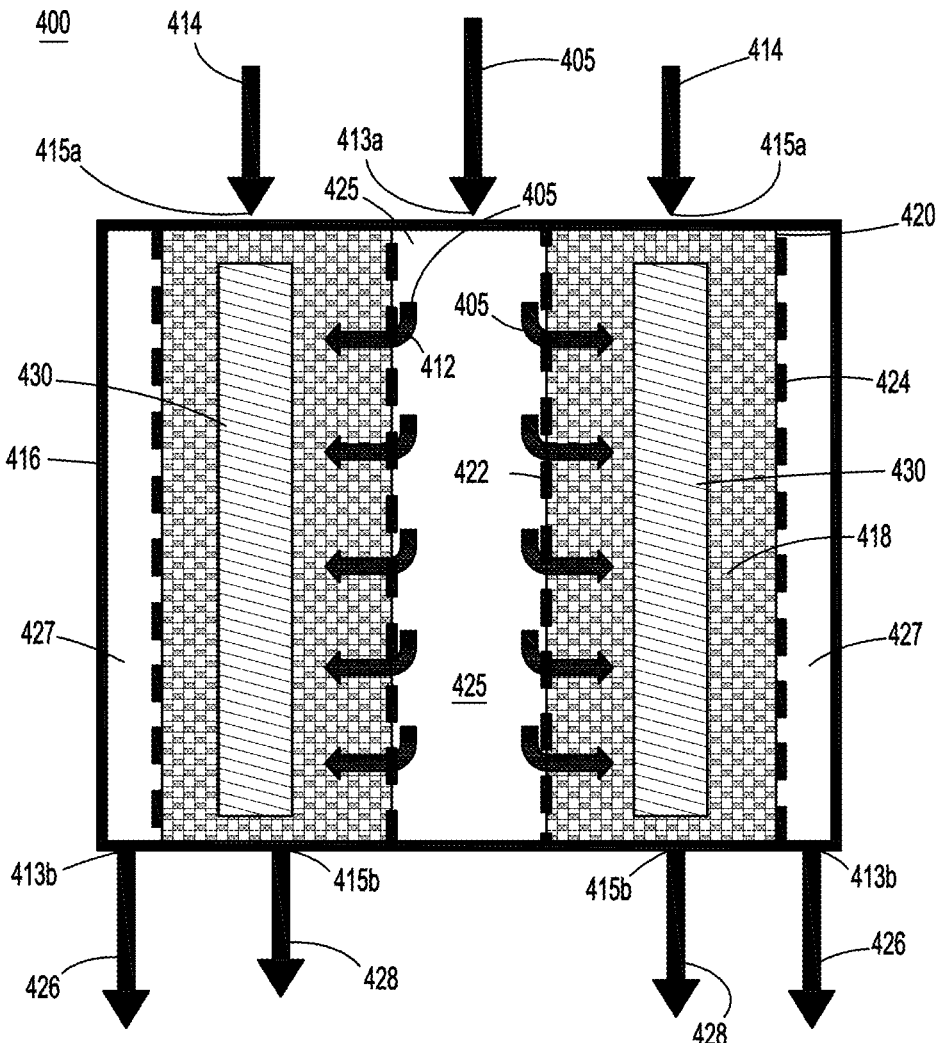
FIG. 5B illustrates a system with a radial flow moving bed reactor with internal heating elements for use in converting
Figure 5C:
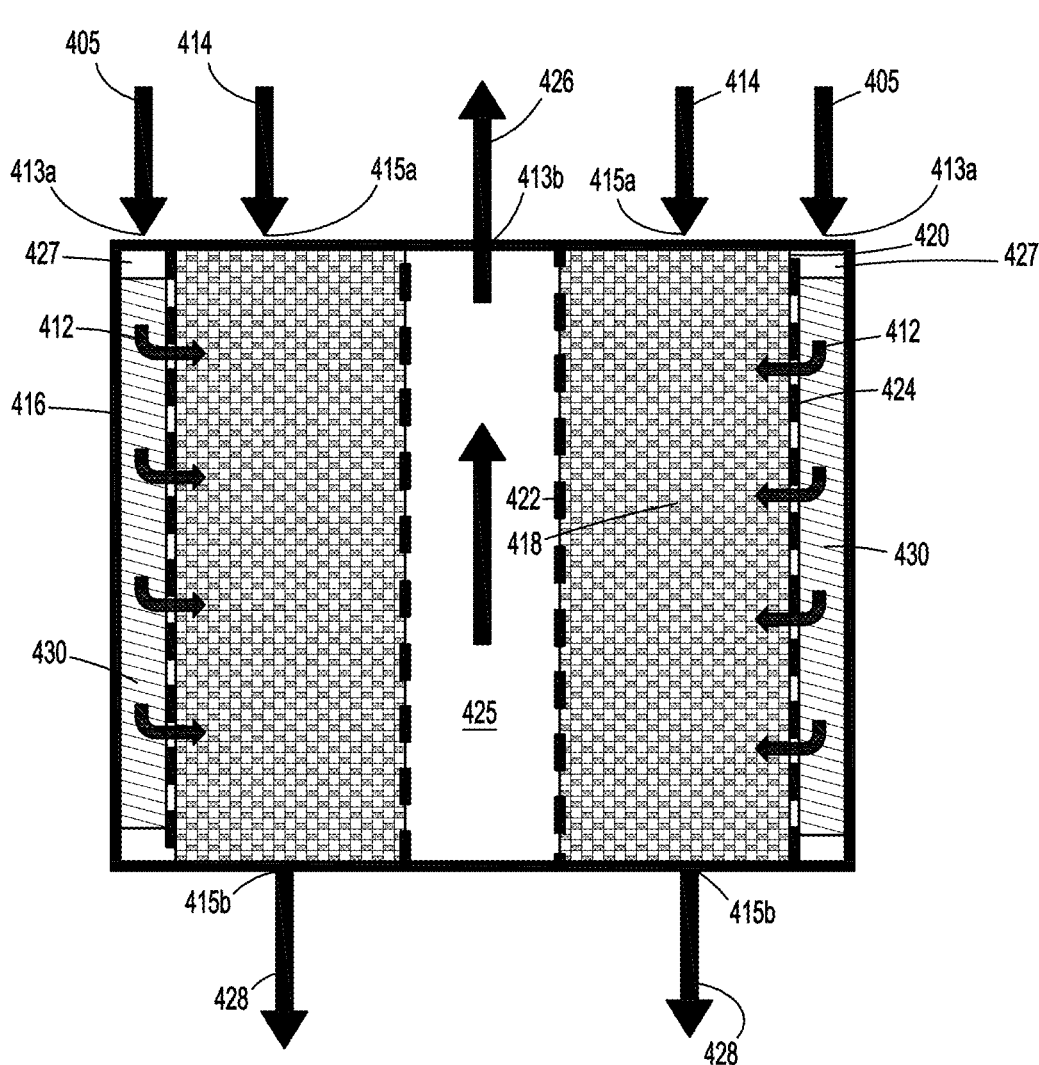

FIG. 5C illustrates a system with a radial flow moving bed reactor with internal heating elements for use in converting a light hydrocarbon feed comprising $C_1$-$C_3$ alkanes to a product effluent stream comprising a $C_2$ to $C_{10}$ hydrocarbon product and hydrogen, according to yet another illustrative embodiment.

Figure 6:
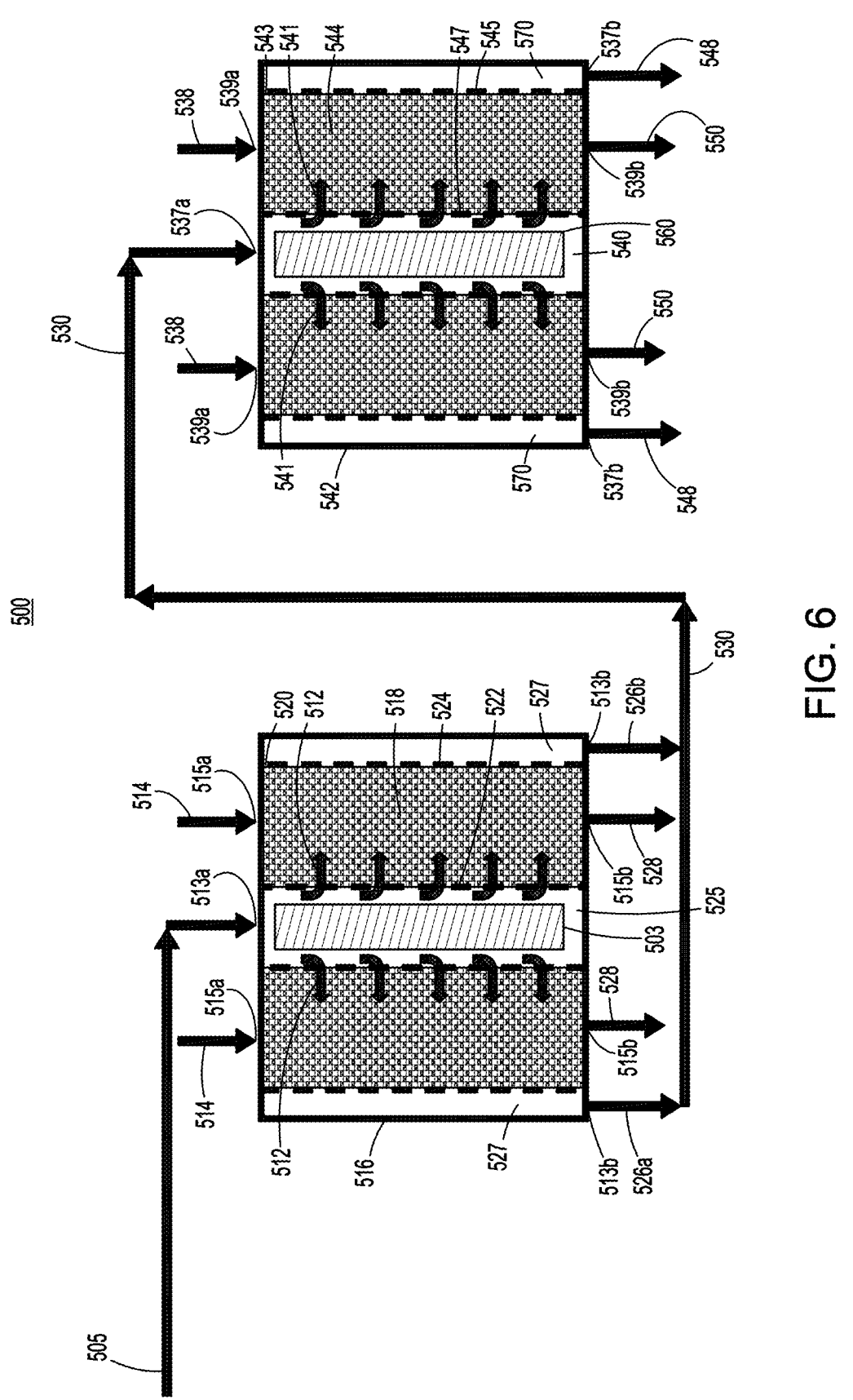

FIG. 6 illustrates a multi-stage reactor system with radial flow moving bed reactors with an internal heating element for use in converting a light hydrocarbon feed comprising $C_1$-$C_3$ alkanes to a product effluent stream comprising a $C_2$ to $C_{10}$ hydrocarbon product and hydrogen, according to an illustrative embodiment.

Figure 7:
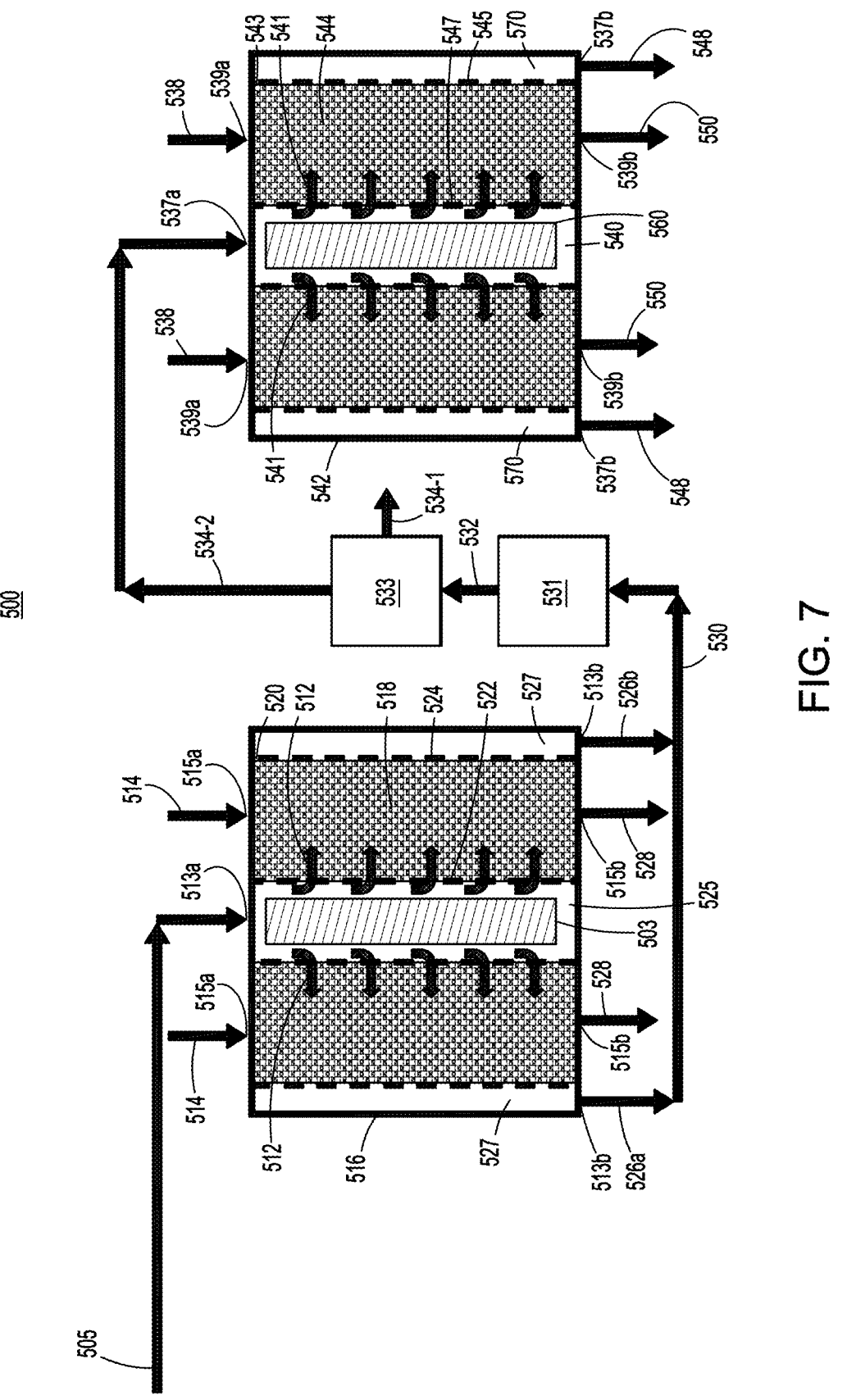

FIG. 7 illustrates a multi-stage reactor system with radial flow moving bed reactors with an internal heating element and an inter-stage product separation unit for use in converting a light hydrocarbon feed comprising $C_1$-$C_3$ alkanes to a product effluent stream comprising a $C_2$ to $C_{10}$ hydrocarbon product and hydrogen, according to an illustrative embodiment.

DETAILED DESCRIPTION

Various illustrative embodiments described herein are directed to radially flowing moving bed reactors and processes for catalytic cracking of light hydrocarbons to chemicals and/or fuels. The conversion of light hydrocarbons into added value chemicals, materials and fuels offers one alternative to crude.

Catalytic cracking of light hydrocarbons such as methane can produce higher molecular weight hydrocarbons, such as olefins, alkynes and aromatics (e.g., benzene), as value-added chemicals and at the same time produce hydrogen that can be used to make, for example, fuel. Hydrogen is one of the more important options for future clean energy. However, the desired product selectivity obtained from the catalytic cracking process will depend on the particular type of catalyst as well as reaction condition. In general, this reaction is highly endothermic, and the exact value of the reaction heat will depend on the desired product distribution, such as enthalpy in the range of about 90 kJ/mol of $CH_4$ or 60 kJ/mol of $H_2$. It is also an equilibrium limited reaction, and high temperatures are usually required to achieve a $CH_4$ conversion that would be practical for a commercial application. For example, to be commercially practical, maintaining a reactor at a temperature range of 600° C. to 1200° C. is required. The equilibrium conversion is also associated with reaction pressure. For example, at a given reaction temperature higher pressure will lead to lower equilibrium conversion.

In addition to the costs associated with such a heat-intensive reaction, the required heat creates other practical challenges. For example, under such temperature conditions, the production of coke or solid carbon in the reactor becomes common, which can negatively affect the yield of valuable products, and can cause plugging of the reactor and catalyst deactivation. Such high temperatures also can require expensive materials for the reactor and can make design of the reactor challenging.

In view of these challenges, there is a need for solutions that produce hydrogen and value-added chemicals from light hydrocarbons in a cost-effective manner. In addition, it would be advantageous for the reactor design for this process to have the capability to (1) provide the reaction heat needed to maintain an optimized temperature profile to achieve high conversion, (2) maintain a low pressure drop to achieve the high conversion, and (3) regenerate and recycle the catalyst being used. It would further be advantageous if such solutions are more energy efficient than existing approaches to produce hydrogen and value-added chemicals.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology can be applied, as long as that definition does not conflict with any other disclosure or definition applied herein or render indefinite or non-enabled any claim to which that definition is applied. To the extent that any definition or usage provided by any document incorporated herein by reference conflicts with the definition or usage provided herein, the definition or usage provided herein controls.

While systems and processes are described in terms of "comprising" various components or steps, the systems and processes can also "consist essentially of" or "consist of" the various components or steps, unless stated otherwise.

The terms "a," "an," and "the" are intended to include plural alternatives, e.g., at least one. The terms "including", "with", and "having", as used herein, are defined as comprising (i.e., open language), unless specified otherwise.

Various numerical ranges are disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. For example, all numerical end points of ranges disclosed herein are approximate, unless excluded by proviso.

Values or ranges may be expressed herein as "about", from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In another aspect, use of the term "about" means ±20% of the stated value, ±15% of the stated value, ±10% of the stated value, ±5% of the stated value, ±3% of the stated value, or ±1% of the stated value.

Applicant reserves the right to proviso out or exclude any individual members of any such group of values or ranges, including any sub-ranges or combinations of sub-ranges within the group, that can be claimed according to a range or in any similar manner, if for any reason Applicant chooses to claim less than the full measure of the disclosure, for example, to account for a reference that Applicant may be unaware of at the time of the filing of the application. Further, Applicant reserves the right to proviso out or exclude any members of a claimed group.

A "fresh catalyst" as used herein denotes a catalyst which has not previously been used in a catalytic process.

A "spent catalyst" as used herein denotes a catalyst that has less activity at the same reaction conditions (e.g., temperature, pressure, inlet flows) than the catalyst had when it was originally exposed to the process. This can be due to a number of reasons, several non-limiting examples of causes of catalyst deactivation are coking or carbonaceous material sorption or accumulation, steam or hydrothermal deactivation, metals (and ash) sorption or accumulation, attrition, morphological changes including changes in pore sizes, cation or anion substitution, and/or chemical or compositional changes.

A "regenerated catalyst" as used herein denotes a catalyst that had become spent, as defined above, and was then subjected to a process that increased its activity to a level greater than it had as a spent catalyst. This may involve, for example, reversing transformations or removing contaminants outlined above as possible causes of reduced activity. The regenerated catalyst typically has an activity that is equal to or less than the fresh catalyst activity.

The term "primarily" shall be understood to mean an amount greater than 50%, e.g., 50.01 to 100%, or any range between, e.g., 51 to 95%, 75% to 90%, at least 60%, at least 70%, at least 80%, etc.

The non-limiting illustrative embodiments described herein overcome the drawbacks discussed above by providing processes for converting a light hydrocarbon feed comprising $C_1$-$C_3$ alkanes to, for example, a product stream comprising a $C_2$ to $C_{10}$ hydrocarbon product and hydrogen by utilizing one or more radial flow moving bed reactors. The non-limiting illustrative embodiments of the present disclosure will be specifically described below with reference to the accompanying drawings. For the purpose of clarity, some steps leading up to the production of the product effluent stream comprising a $C_2$ to $C_{10}$ hydrocarbon product and hydrogen as illustrated in FIGS. 1-7 may be omitted. In other words, one or more well-known processing steps which are not illustrated but are well-known to those of ordinary skill in the art have not been included in the figures. This is not intended to be interpreted as a limitation of any particular embodiment, or illustration, or scope of the claims.

General Process

The non-limiting illustrative embodiments described herein are directed to a process for converting a light hydrocarbon feed comprising primarily $C_1$-$C_3$ alkanes to a $C_2$ to $C_{10}$ hydrocarbon product and hydrogen utilizing one or more radial flow moving bed reactors. In non-limiting illustrative embodiments, the process involves at least flowing a catalyst composition comprising catalyst particles into a radial flow moving bed reactor, wherein the catalyst particles move by gravity through the radial flow moving bed reactor to an exit point of the radial flow moving bed reactor, wherein the catalyst particles form a moving catalyst bed in the radial flow moving bed reactor, flowing a light hydrocarbon feed stream comprising $C_1$ to $C_3$ alkanes into the radial flow moving bed reactor in a manner so that the light hydrocarbon feed stream flows radially inward or radially outward through the moving catalyst bed and thereby contacts the catalyst particles under reaction conditions to produce a product effluent stream comprising a $C_2$ to $C_{10}$ hydrocarbon product and hydrogen, and flowing the product effluent stream from the radial flow moving bed reactor.

The $C_1$-$C_3$ alkanes are not particularly limited and may include, for example, natural gas, methane, ethane, propane, and mixtures thereof. As used herein, natural gas comprises methane and potentially higher alkanes, carbon dioxide, nitrogen or other gases, and/or sulfide compounds such as hydrogen sulfide, and mixtures thereof. In illustrative embodiments, the light hydrocarbon feed may further contain a portion of the produced products that are recycled back to the light hydrocarbon feed along with unreacted methane. The produced product typically comprises a $C_2$ to $C_{10}$ hydrocarbon product and hydrogen. The $C_2$ to $C_{10}$ hydrocarbon product is not particularly limited and can be, for example, saturated, unsaturated, aromatic, or a mixture of such compounds. Examples of aromatic hydrocarbons include benzene, toluene, xylene, naphthalene, and methylnaphthalene. In some embodiments the $C_2$ to $C_{10}$ hydrocarbon product may comprise ethylene, propylene, acetylene, benzene, naphthalene, and various mixtures thereof depending upon the desired products and reactions used. In addition, as one skilled in the art will ready appreciate, the resulting $C_2$ to $C_{10}$ hydrocarbon product can be one of a liquid $C_2$ to $C_{10}$ hydrocarbon product or a solid $C_2$ to $C_{10}$ hydrocarbon product depending on the particular methane conversion process.

As will be discussed below, the light hydrocarbon feed comprising primarily $C_1$-$C_3$ alkanes is heated either before passing into the radial flow moving bed reactor or when in the radial flow moving bed reactor under suitable conditions in the presence of the catalyst to produce a $C_2$ to $C_{10}$ hydrocarbon product and hydrogen. Suitable conditions may vary depending upon the reactants, desired products, catalysts, and equipment employed. In illustrative embodiments, a temperature can be from about 500° C., or from about 700° C., and up to about 1000° C. or up to about 1200° C., and a pressure of from about 1 atmosphere up to about 3, or up to about 5, or up to about 10 may be employed to produce a $C_2$ to $C_{10}$ hydrocarbon product and hydrogen.

Catalyst

In an illustrative embodiment, as may be combined with one or more of the preceding paragraphs, the catalyst for the radial flow moving bed reactor is circulated through the unit in a continuous manner between catalytic cracking reaction and regeneration while continuously maintaining the cracking catalyst in the radial flow moving bed reactor. In illustrative embodiments, the catalyst for use herein can be any cracking catalyst suitable for a radial flow moving bed reactor. The catalyst composition, form, size, shape, and properties may vary depending upon such parameters as the reactants, reactor type, tube size and shape, reaction conditions, and/or desired products. In some embodiments the catalyst comprises substantially spheric pellets. In some embodiments the catalyst comprises substantially spheric pellets having a diameter of about 1 to about 10 millimeters (mm). In some embodiments the catalyst comprises substantially spheric pellets having a diameter of about 2 to about 5 mm.

In non-limiting illustrative embodiments, a catalyst for use herein may comprise fused silica, quartz, glass, a zeolite, $Si_3N_4$, SiC, $SiC_xO_y$, wherein 4x+2y=4, $SiO_aN_b$, wherein 2a+3b=4, BN, $TiO_2$, $ZrO_2$, $Al_2O_3$, $CeO_2$, $Nb_2O_5$, $La_2O_3$, a perovskite, or any mixture thereof; and a metal dopant embedded in the matrix wherein the metal dopant comprises Fe, Ni, Co, Cu, Zn, Mn, or any mixture thereof; with the proviso that the catalyst is not the product of fusing ferrous metasilicate with $SiO_2$ at a temperature of 500° C. to 2400° C.

Reactor Systems

Figure 1:
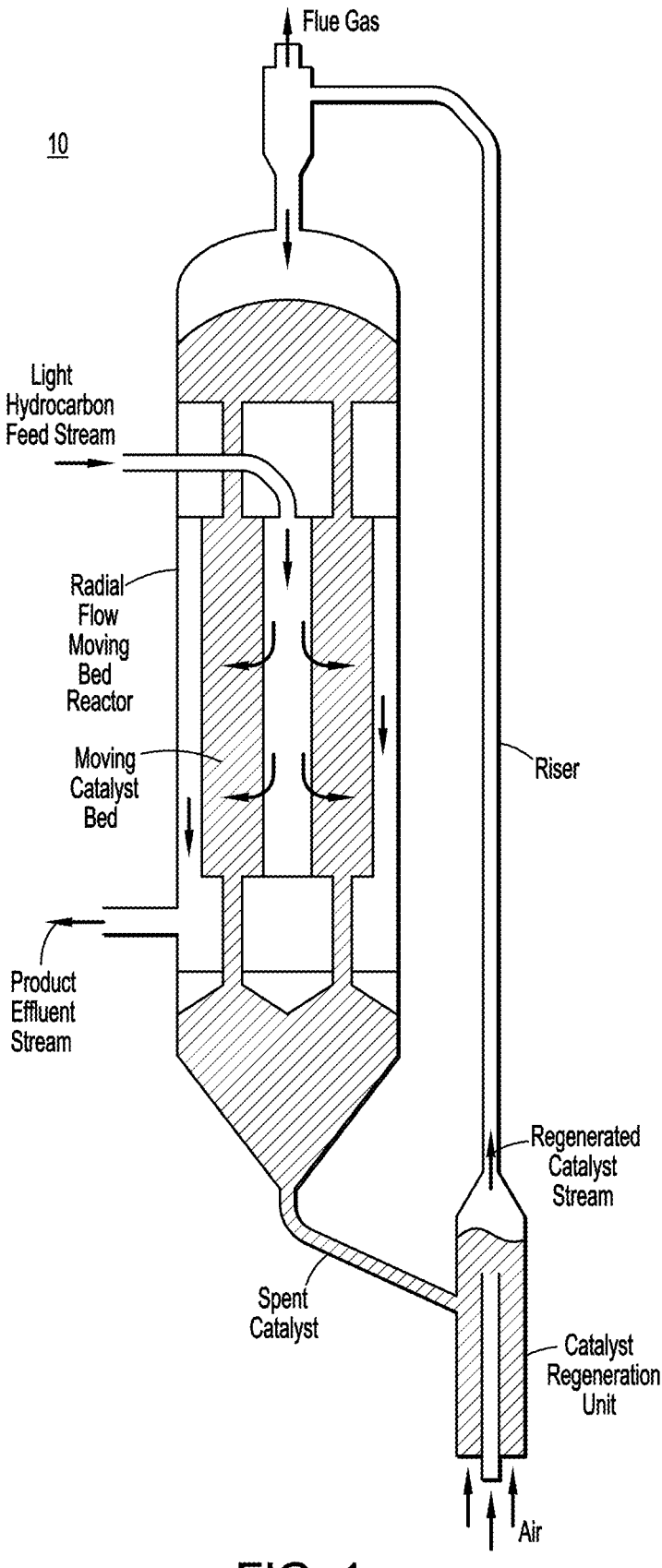
FIG. 1 illustrates a schematic diagram of a system with a radial flow moving bed reactor combined with a riser-type catalyst regeneration unit for use in converting a light hydrocarbon feed comprising $C_1$-$C_3$ alkanes to a product effluent stream comprising a $C_2$ to $C_{10}$ hydrocarbon product and hydrogen, according to an illustrative embodiment.

The non-limiting illustrative embodiments of the present disclosure, as may be combined with one or more of the preceding paragraphs, will now be further described with reference to the drawings. Referring now to the drawings in more detail, FIG. 1 illustrates system 10 including a radial flow moving bed reactor, a catalyst regeneration unit and a riser external to the radial flow moving bed reactor. It is to be understood that system 10 including radial flow moving bed reactor, catalyst regeneration unit and riser are not limited to the configuration of the embodiments shown in FIG. 1, and other configurations are contemplated herein.

In general, the radial flow moving bed reactor depicts where the light hydrocarbon feed stream could be introduced into the radial flow moving bed reactor. Although only one injection point in the radial flow moving bed reactor is shown for the light hydrocarbon feed stream, it is to be understood that the radial flow moving bed reactor can be designed to have two or more feedstock injection points, namely, at least one for one the light hydrocarbon feed stream and at least one for another the light hydrocarbon feed stream. As described below with regard to FIGS. 2A-7, system 10 can further include one or more heating units, either external to the radial flow moving bed reactor or located within the radial flow moving bed reactor, for heating the light hydrocarbon feed stream. The catalyst stream comprising catalyst particles is injected into the top of the radial flow moving bed reactor from catalyst regeneration unit via the riser as a hot regenerated catalyst stream as discussed below, i.e., a regenerated catalyst stream is at an elevated temperature relative to the temperature of the spent catalyst.

In illustrative embodiments, the light hydrocarbon feed stream and the hot regenerated catalyst stream are subjected to reaction conditions as discussed below, e.g., a temperature of from about 500° C. to about 1200° C., a pressure drop across the radial flow moving bed reactor of from about 1 to about 10 psi, or from about 1 to about 3 psi; and for a residence time of the light hydrocarbon feed stream in the radial flow moving bed reactor of from about 0.05 seconds to about 100 seconds, or from about 0.1 seconds to about 2 seconds.

During the reaction, coke will be formed in the radial flow moving bed reactor, catalytically or thermally, when the light hydrocarbon feed stream is in contact with the hot regenerated catalyst stream. The coke formed can be deposited on the surface of the hot regenerated catalyst stream, thereby forming spent catalyst comprising the catalyst particles and coke deposits, i.e., coked-catalyst particulates. The spent catalyst is continuously introduced to the catalyst regeneration unit where the spent catalyst is subjected to coke burning conditions to burn most, if not all, of the coke from the spent catalyst and provide another hot regenerated catalyst stream. The coke can be burned from the spent catalyst by exposing the spent catalyst to a stream such as an oxygen-containing gas stream, e.g., an inert gas/air stream, at appropriate high temperature and time duration conditions to burn off and remove substantially all coke deposits from the catalyst. In an illustrative embodiment, a temperature can range from about 450° C. to about 1400° C., and a time period can range from about 5 to about 600 minutes. Accordingly, regenerating the spent catalyst generally comprises combustion of the spent catalyst in an oxidizing atmosphere to burn the coke deposits and redisperse active metal on the catalyst particles. Burning the coke is an exothermic process that can supply the heat needed for the reaction process. In a heat balanced operation, the quantity of coke formed on the catalyst is significant enough that no external heat source or fuel is needed to supplement the heat from coke combustion.

The coke burn causes the spent catalyst to be heated to an elevated temperature, e.g., a temperature of from about 450° C. to about 1400° C., to provide a hot regenerated catalyst stream relatively free or free of coke wherein the catalyst particles are heated. The hot regenerated catalyst stream is continuously introduced to the radial flow moving bed reactor where it moves downward by gravity. The heat generated by the coke burn in the catalyst regeneration unit is continuously transferred with the hot regenerated catalyst stream to the radial flow moving bed reactor via the riser. During the coke burn, the flue gas is continuously passed out of the catalyst regeneration unit via the riser.

An alternative embodiment of regenerating the catalyst is by injecting super-heated steam to the riser where coke deposit on the catalysts is gasified by reaction with the steam thereby producing carbon monoxide, carbon dioxide and hydrogen.

The gravity flow of the regenerated catalyst stream from the entrance of the radial flow moving bed reactor to its exit point in the radial flow moving bed reactor through the moving catalyst bed, and the radial flow of the light hydrocarbon feed stream involves flowing the light hydrocarbon feed stream into the radial flow moving bed reactor in a manner such that the light hydrocarbon feed stream flows radially inward or radially outward through the moving catalyst bed and thereby contacts the regenerated catalyst stream under reaction conditions to produce a product effluent stream composed of at least a $C_2$ to $C_{10}$ hydrocarbon product and hydrogen. In this way, the light hydrocarbon feed stream flows perpendicularly or substantially perpendicularly to the movement of the regenerated catalyst stream in the radial flow moving bed reactor. The moving catalyst bed, according to illustrative embodiments of the present disclosure, has the regenerated catalyst stream moving relatively slowly. The moving catalyst bed implemented herein can therefore provide high production capacity without increased pressure drop or increased vessel size while the regenerated catalyst stream remains at an acceptable activity level by continuously replenishing regenerated catalyst stream.

Referring now to the FIGS. 2A-7, non-limiting illustrative embodiments of a radial flow moving bed reactor system for use in the system 10 of FIG. 1 for converting a light hydrocarbon feed comprising primarily $C_1$-$C_3$ alkanes to a $C_2$ to $C_{10}$ hydrocarbon product and hydrogen utilizing one or more radial flow moving bed reactors will now be described. It is to be understood that the system including the one or more radial flow moving bed reactors are not limited to the configuration of the embodiments shown in FIGS. 2A-7, and other configurations are contemplated herein.

Figure 2A:
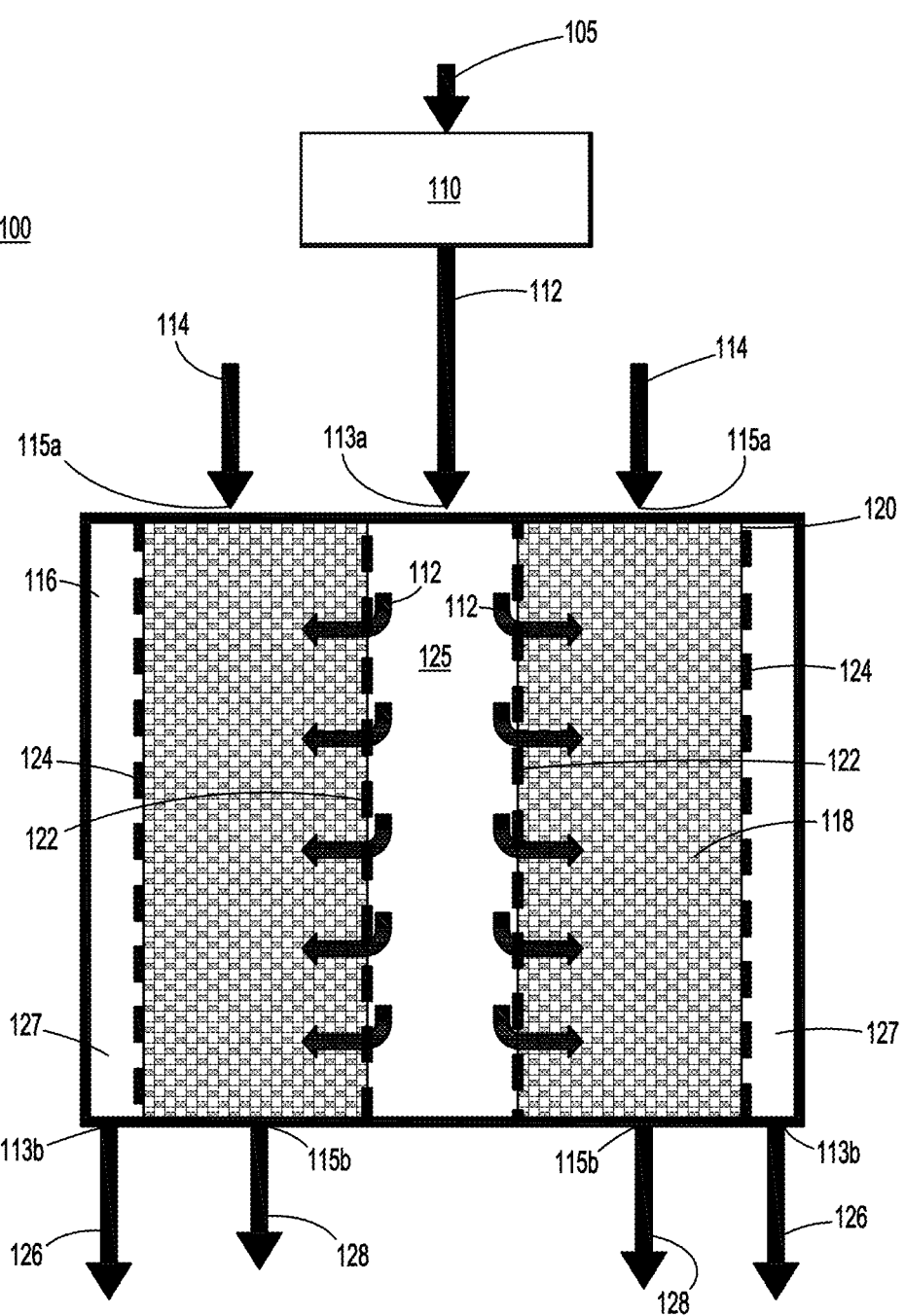
FIG. 2A illustrates a system with a radial flow moving bed reactor and an external heating element for converting a light hydrocarbon feed comprising $C_1$-$C_3$ alkanes to a product effluent stream comprising a $C_2$ to $C_{10}$ hydrocarbon product and hydrogen, according to an illustrative embodiment.
Figure 2B:
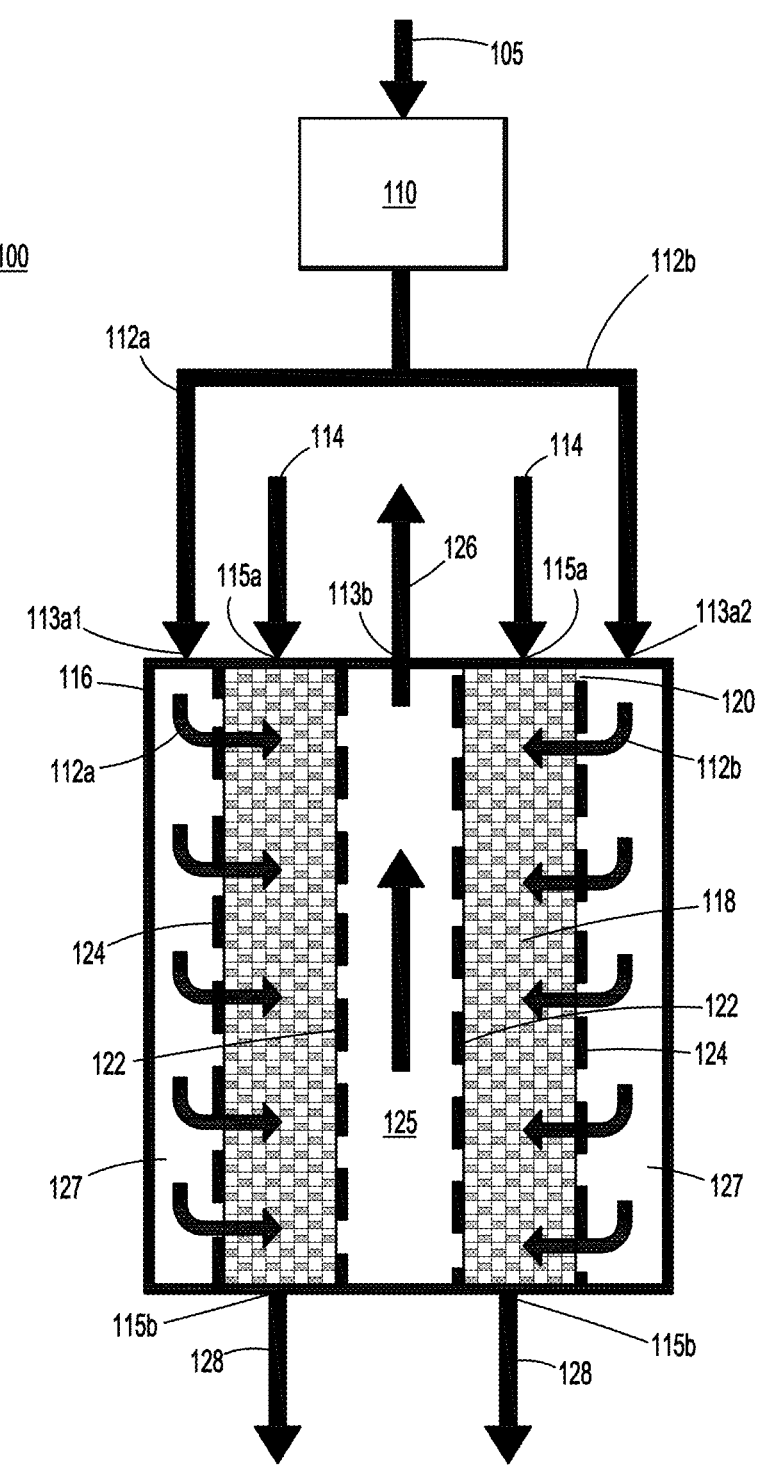
FIG. 2B illustrates a system with a radial flow moving bed reactor and an external heating element for converting a light hydrocarbon feed comprising $C_1$-$C_3$ alkanes to a product effluent stream comprising a $C_2$ to $C_{10}$ hydrocarbon product and hydrogen, according to another illustrative embodiment.

FIGS. 2A and 2B illustrate system 100 including heating unit 110 and radial flow moving bed reactor 116. System 100 may include one or more radial flow moving bed reactors arranged in series or parallel for cracking the light hydrocarbon feed to form a $C_2$ to $C_{10}$ hydrocarbon product and hydrogen. While the exemplary embodiments are described in FIGS. 2A and 2B with system 100 having one radial flow moving bed reactor, it is to be appreciated that any number of radial flow moving bed reactors arranged in series or parallel are contemplated herein. For example, illustrative embodiments of present disclosure may have 1, 2, 3, 4, 5, 6, or 7 radial flow moving bed reactors arranged in series or parallel.

System 100 includes heating unit 110 for heating light hydrocarbon feed 105 prior to entering radial flow moving bed reactor 116 as heated light hydrocarbon feed stream 112 via injection point 113a. Heating unit 110 can be any suitable heating unit capable of heating light hydrocarbon feed 105 to a desired temperature to carry the thermal energy necessary for the endothermic reactions that take place inside the moving catalyst bed 118. For example, a suitable temperature for converting the light hydrocarbon feed to a $C_2$ to $C_{10}$ hydrocarbon product and hydrogen in radial flow moving bed reactor 116 can be as discussed above, i.e., a temperature from about 500° C., or from about 700° C., and up to about 1000° C. or up to about 1200° C.

In some embodiments, heating unit 110 is an electrical heater, and may include a heating element, such as a resistive or inductive heating element. The heating unit 110 is configured to heat the light hydrocarbon feed 105 to the desired temperature for being converted to a $C_2$ to $C_{10}$ hydrocarbon product and hydrogen in radial flow moving bed reactor 116. The temperature profile can be further tailored by adjusting the amount of power supplied to the electric heater.

In another alternate embodiment, the heating unit 110 may include a heat exchanger configured to heat the light hydrocarbon feed 105 using heat extracted from a high-temperature fluid, such as a fluid heated up to about 1200° C. or more. This fluid may be provided from a solar concentrator farm or a power plant. In some embodiments, the heating unit 110 may include multiple heater zones with independent power levels (divided vertically or circumferentially or both), in order to enhance thermal uniformity. In some embodiments, the heat exchanger may be a shell-and-tube, plate-fin, microchannel, spiral wound, or any other suitable heat exchanger.

As discussed above, system 100 includes radial flow moving bed reactor 116, in which heated light hydrocarbon feed stream 112 flows radially through radial flow moving bed reactor 116 while regenerated catalyst stream 114 moves vertically downward through radial flow moving bed reactor 116. In this way, heated light hydrocarbon feed stream 112 flows perpendicularly or substantially perpendicularly to the movement of regenerated catalyst stream 114 in radial flow moving bed reactor 116. FIG. 2A illustrates radial flow moving bed reactor 116 as an outward flowing radial flow moving bed reactor.

To implement this perpendicular or substantially perpendicular flow, the process may involve allowing particles of regenerated catalyst stream 114 to enter radial flow moving bed reactor 116 at injection points 115a and move slowly by gravity through the radial flow moving bed reactor 116 to the exit points 115b of radial flow moving bed reactor 116. The injection points 115a of the radial flow moving bed reactor 116 are vertically above the exit points 115b of radial flow moving bed reactor 116. The movement, by gravity, of particles of regenerated catalyst stream 114 from the injection points 115a to exit points 115b of radial flow moving bed reactor 116 forms a moving catalyst bed in radial flow moving bed reactor 116.

In some embodiments, regenerated catalyst stream 114 will be heated to a desired temperature to carry the thermal energy necessary for the endothermic reactions of the heated light hydrocarbon feed stream 112 that take place inside the moving catalyst bed 118. In some embodiments, regenerated catalyst stream 114 can be a heated regenerated catalyst stream when leaving the riser-type catalyst regeneration unit as discussed above.

Radial flow moving bed reactor 116 includes moving catalyst bed 118 formed by flowing a catalyst composition comprising catalyst particles from regenerated catalyst stream 114 through injection points 115a at the upper portion of radial flow moving bed reactor 116 so that the catalyst flows downward through perforated container 120.

Perforated container 120, according to embodiments of the present disclosure, is adapted so that it keeps the catalyst particles contained within perforated container 120, while allowing heated light hydrocarbon feed stream 112 to be able to flow into perforated container 120 and contact moving catalyst bed 118. Thus, the perforations in perforated walls 122 and 124 may be large enough to have sufficient flow of heated light hydrocarbon feed stream 112 through, but small enough such that the catalyst particles are contained within perforated container 120. Heated light hydrocarbon feed stream 112 flows into region 125 via injection point 113a and then through perforated wall 122 to enter and make contact with moving catalyst bed 118. A product effluent stream 126 comprising a $C_2$ to $C_{10}$ hydrocarbon product and hydrogen is formed as a result of heated light hydrocarbon feed stream 112 contacting moving catalyst bed 118 in radial flow moving bed reactor 116 under reaction conditions as discussed below that are sufficient to crack the light hydrocarbons in heated light hydrocarbon feed stream 112. According to some embodiments, radial flow moving bed reactor 116 has region 127 for receiving product effluent stream 126 from the moving catalyst bed 118, as it exits perforated container 120 through perforated wall 124.

By providing both a heated catalyst stream and a heated light hydrocarbon feed stream to radial flow moving bed reactor 116, these streams can carry the thermal energy necessary for the endothermic reactions of the heated light hydrocarbon feed stream 112 that take place inside the moving catalyst bed 118 to allow for the radial flow moving bed reactor 116 to be operated adiabatically, i.e., no additional heat is provided to the radial flow moving bed reactor 116. The heated light hydrocarbon feed stream 112 thereafter exits radial flow moving bed reactor 116 via exit point 113b as product effluent stream 126, i.e., a $C_2$ to $C_{10}$ hydrocarbon product and hydrogen, that is then sent downstream for further processing. The regenerated catalyst stream 114 exits radial flow moving bed reactor 116 via exit points 115b as spent catalyst stream 128 and is sent to a riser-type catalyst regeneration unit for regeneration as discussed above in reference to FIG. 1.

For example, the riser-type catalyst regeneration unit regenerates spent catalyst stream 128 to form another regenerated catalyst stream for sending back to radial flow moving bed reactor 116 as regenerated catalyst stream 114. The regeneration process may involve burning off carbon deposits (coke) on spent catalyst stream 128 in the riser-type catalyst regeneration unit by the application of heat and air. In some embodiments, an amount of fresh catalyst may be added to supplement regenerated catalyst stream 114. In the event that an amount of fresh catalyst is added to supplement regenerated catalyst stream 114, the fresh catalyst can be preheated to a desired temperature to carry the thermal energy necessary for the endothermic reactions of the heated light hydrocarbon feed stream 112 that takes place inside the moving catalyst bed 118.

The gravity flow of regenerated catalyst stream 114 from injection points 115a of radial flow moving bed reactor 116 to exit points 115b of radial flow moving bed reactor 116 through moving catalyst bed 118, and the radial flow of heated light hydrocarbon feed stream 112 involve flowing heated light hydrocarbon feed stream 112 into radial flow moving bed reactor 116 in a manner such that heated light hydrocarbon feed stream 112 flows radially outward through the moving catalyst bed 118 and thereby contacts the catalyst particles under reaction conditions to produce a $C_2$ to $C_{10}$ hydrocarbon product and hydrogen. The moving catalyst bed 118, according to illustrative embodiments of the present disclosure, has regenerated catalyst stream 114 moving relatively slowly. In this way, the moving catalyst bed 118 implemented herein can provide high production capacity without increased pressure drop or increased vessel size while the regenerated catalyst stream 114 remains at an acceptable activity level by continuously replenishing regenerated catalyst stream 114.

In an illustrative embodiment, a pressure drop across the radial flow moving bed reactor 116, i.e., the pressure difference between the injection point 113*a* of heated light hydrocarbon feed stream 112 in radial flow moving bed reactor 116 to the exit points 113*b* of heated light hydrocarbon feed stream 112 in radial flow moving bed reactor 116, can range from about 1 psi to about 10 psi. In an illustrative embodiment, a pressure drop across the radial flow moving bed reactor 116 can range from about 1 psi to about 3 psi. In an illustrative embodiment, a velocity of the regenerated catalyst stream 114 in the radial flow moving bed reactor 116 can be less than about 1 m/s, or less than about 0.5 m/s, e.g., from about 0.001 m/s to about 1 m/s, or to about 0.5 m/s, and a pressure drop across the radial flow moving bed reactor 116 can range from about 1 psi to about 10 psi. In an illustrative embodiment, a velocity of the regenerated catalyst stream 114 in the radial flow moving bed reactor 116 can be less than about 1 m/s, or less than about 0.5 m/s, e.g., from about 0.001 m/s to about 1 m/s, or to about 0.5 m/s, and a pressure drop across the radial flow moving bed reactor 116 can range from about 1 psi to about 3 psi.

The reaction time inside radial flow moving bed reactor 116 can be controlled by adjusting the flow rate of the heated light hydrocarbon feed stream 112 through the radial flow moving bed reactor 116 to achieve a relatively high conversion and relatively high selectivity. The desired reaction time will depend on the particular catalyst employed and its performance. In an illustrative embodiment, a suitable reaction time is from about 0.05 seconds to about 100 seconds. In an illustrative embodiment, a suitable reaction time is from about 0.1 seconds to about 3 seconds.

With regard to FIG. 2B, FIG. 2B is an alternative embodiment of FIG. 2A and illustrates radial flow moving bed reactor 116 as an inward flowing radial flow moving bed reactor. System 100 includes heating unit 110 and radial flow moving bed reactor 116, in which light hydrocarbon feed 105 is heated in a similar manner and a similar temperature as discussed above and is split into heated light hydrocarbon feed stream 112*a* and heated light hydrocarbon feed stream 112*b*. Heated light hydrocarbon feed streams 112*a* and 112*b* flow radially through radial flow moving bed reactor 116 while regenerated catalyst stream 114 moves vertically downward through radial flow moving bed reactor 116. In this way, heated light hydrocarbon feed streams 112*a* and 112*b* flow perpendicularly or substantially perpendicularly to the movement of regenerated catalyst stream 114 in radial flow moving bed reactor 116 as discussed above.

Radial flow moving bed reactor 116 includes moving catalyst bed 118 formed by flowing a catalyst composition comprising catalyst particles from regenerated catalyst stream 114 through injection points 115*a* at the upper portion of radial flow moving bed reactor 116 so that the catalyst flows downward through perforated container 120 to exit points 115*b*. Heated light hydrocarbon feed streams 112*a* and 112*b* flow into region 127 via respective injection points 113*a*1 and 113*a*2 and then through perforated wall 124 to enter and make contact with moving catalyst bed 118. As a result of heated light hydrocarbon feed streams 112*a* and 112*b* contacting moving catalyst bed 118 in radial flow moving bed reactor 116 under reaction conditions discussed above sufficient to crack the light hydrocarbons in heated light hydrocarbon feed streams 112*a* and 112*b*, product effluent stream 126 comprising a $C_2$ to $C_{10}$ hydrocarbon product and hydrogen is formed. According to some embodiments, radial flow moving bed reactor 116 has region 125 for receiving product effluent stream 126 from the moving catalyst bed 118, as it exits perforated container 120 through perforated wall 122.

By providing both a heated catalyst stream and a heated light hydrocarbon feed stream to radial flow moving bed reactor 116, these streams can carry the thermal energy necessary for the endothermic reactions of the heated light hydrocarbon feed streams 112*a* and 112*b* that take place inside the moving catalyst bed 118 to allow for the radial flow moving bed reactor 116 to be operated adiabatically, i.e., no additional heat is provided to the radial flow moving bed reactor 116. The heated light hydrocarbon feed streams 112*a* and 112*b* thereafter exit radial flow moving bed reactor 116 via exit point 113*b* as product effluent stream 126, i.e., a $C_2$ to $C_{10}$ hydrocarbon product and hydrogen, that is then sent downstream for further processing. The regenerated catalyst stream 114 exits radial flow moving bed reactor 116 via exit points 115*b* as spent catalyst stream 128 and is sent to a riser-type catalyst regeneration unit for regeneration as discussed above in reference to FIG. 1.

The gravity flow of regenerated catalyst stream 114 from an upper portion of radial flow moving bed reactor 116 to a lower portion of radial flow moving bed reactor 116 through moving catalyst bed 118 and the radial flow of heated light hydrocarbon feed streams 112*a* and 112*b* involve flowing heated light hydrocarbon feed streams 112*a* and 112*b* into radial flow moving bed reactor 116 in a manner such that heated light hydrocarbon feed streams 112*a* and 112*b* flow radially inward through the moving catalyst bed 118 and thereby contacts the catalyst particles under reaction conditions to produce a $C_2$ to $C_{10}$ hydrocarbon product and hydrogen. The moving catalyst bed 118, according to illustrative embodiments of the present disclosure, has regenerated catalyst stream 114 moving slowly. In this way, the radial flow moving catalyst bed implemented herein can provide high production capacity without increased pressure drop or increased vessel size while the regenerated catalyst stream 114 remains at an acceptable activity level, by continuous catalyst renewal.

In an illustrative embodiment, the pressure drop across the radial flow moving bed reactor 116, velocity of the regenerated catalyst stream 114 in the radial flow moving bed reactor 116 and reaction times inside radial flow moving bed reactor 116 can be the same as those discussed above.

Figure 3:
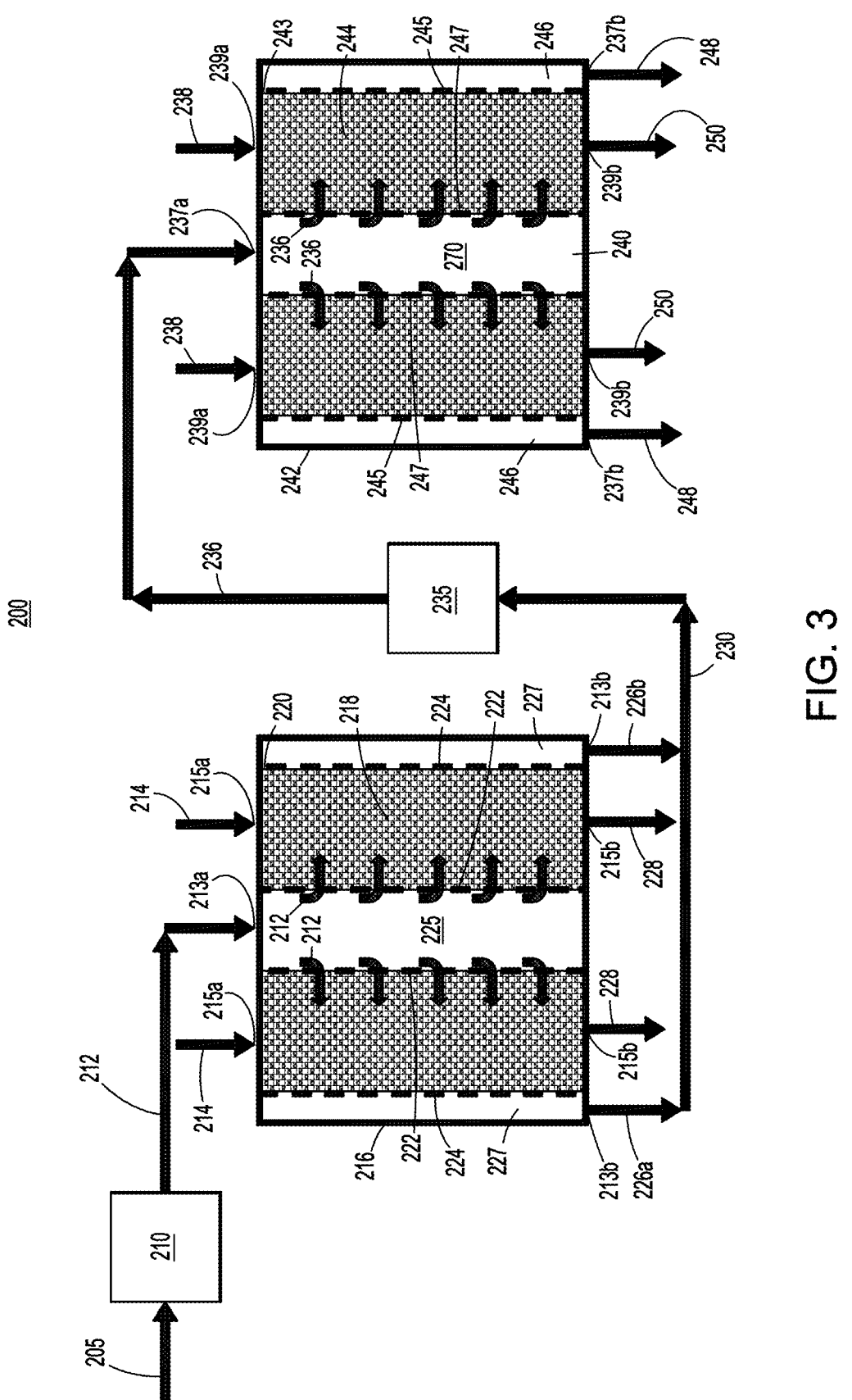
FIG. 3 illustrates a multi-stage reactor system with radial flow moving bed reactors and external heating elements for use in converting a light hydrocarbon feed comprising $C_1$-$C_3$ alkanes to a product effluent stream comprising a $C_2$ to $C_{10}$ hydrocarbon product and hydrogen, according to an alternative illustrative embodiment.

In one or more additional illustrative embodiments, as may be combined with the preceding paragraphs, FIG. 3 illustrates multi-stage reactor system 200 including radial flow moving bed reactors 216 and 242 with respective heating units 210 and 235. Radial flow moving bed reactors 216 and 242 are similar to radial flow moving bed reactor 116 as discussed above for FIG. 2A, i.e., as an outward flowing radial flow moving bed reactor. However, the multi-stage reactor system 200 of the present disclosure is not limited to such a configuration and any combination of outward and inward flowing radial flow moving bed reactors are contemplated herein.

Multi-stage reactor system 200 includes heating unit 210 for heating light hydrocarbon feed 205 prior to entering radial flow moving bed reactor 216 as heated light hydrocarbon feed stream 212 via injection point 213*a*. Heating unit 210 can be any suitable heating unit capable of heating light hydrocarbon feed 205 to a desired temperature to carry the thermal energy necessary for the endothermic reactions that take place inside the moving catalyst bed 218 as discussed above for heating unit 110.

Multi-stage reactor system 200 further includes radial flow moving bed reactor 216, in which heated light hydrocarbon feed stream 212 flows radially through radial flow moving bed reactor 216 while regenerated catalyst stream 214 moves vertically downward through radial flow moving bed reactor 216 via injection point 215a. In this way, heated light hydrocarbon feed stream 212 flows perpendicularly or substantially perpendicularly to the movement of regenerated catalyst stream 214 in radial flow moving bed reactor 216 as discussed above for heated light hydrocarbon feed stream 112 and regenerated catalyst stream 114.

In some embodiments, regenerated catalyst stream 214 will be heated to a desired temperature to carry the thermal energy necessary for the endothermic reactions of the heated light hydrocarbon feed stream 212 that take place inside the moving catalyst bed 218 as discussed above for regenerated catalyst stream 114.

Radial flow moving bed reactor 216 includes moving catalyst bed 218 formed by flowing a catalyst composition comprising catalyst particles from regenerated catalyst stream 214 through injection points 215a at the upper portion of radial flow moving bed reactor 216 so that the catalyst flows downward through perforated container 220. Heated light hydrocarbon feed stream 212 flows into region 225 via injection point 213a and then through perforated wall 222 to enter and make contact with moving catalyst bed 218. As a result of heated light hydrocarbon feed stream 212 contacting moving catalyst bed 218 in radial flow moving bed reactor 216 under reaction conditions as discussed above sufficient to crack the light hydrocarbons in heated light hydrocarbon feed stream 212, product effluent streams 226a and 226b comprising a $C_2$ to $C_{10}$ hydrocarbon product and hydrogen is formed. According to some embodiments, radial flow moving bed reactor 216 has region 227 for receiving product effluent streams 226a and 226b from the moving catalyst bed 218, as it exits perforated container 220 through perforated wall 224.

As discussed above for system 100 shown in FIG. 2A, by providing both a heated catalyst stream and a heated light hydrocarbon feed stream to radial flow moving bed reactor 216, these streams can carry the thermal energy necessary for the endothermic reactions of the heated light hydrocarbon feed stream 212 that take place inside the moving catalyst bed 218 to allow for the radial flow moving bed reactor 216 to be operated adiabatically, i.e., no additional heat is provided to the radial flow moving bed reactor 216. The heated light hydrocarbon feed stream 212 thereafter exits radial flow moving bed reactor 216 via exit point 213b as product effluent streams 226a and 226b, i.e., a $C_2$ to $C_{10}$ hydrocarbon product and hydrogen, and the regenerated catalyst stream 214 exits radial flow moving bed reactor 216 via exit point 215b as spent catalyst stream 228 and is sent to a riser-type catalyst regeneration unit for regeneration as discussed above in reference to FIG. 1.

Following cracking of the heated light hydrocarbon feed stream 212, the product effluent streams 226a and 226b can contain an amount of uncracked heated light hydrocarbon feed stream 212. Accordingly, in some embodiments, product effluent streams 226a and 226b exit via exit points 213b and are combined as product effluent stream 230. Product effluent stream 230 is thereafter sent to heating unit 235 to be further heated to a temperature as discussed above for heated light hydrocarbon feed stream 112. Heating unit 235 can be any suitable heating unit capable of heating product effluent stream 230 to a desired temperature to carry the thermal energy necessary for the endothermic reactions that take place inside the moving catalyst bed 244 as discussed above for heating unit 110.

Multi-stage reactor system 200 further includes radial flow moving bed reactor 242, in which heated product effluent stream 236 flows radially through radial flow moving bed reactor 242 while regenerated catalyst stream 238 moves vertically downward through radial flow moving bed reactor 242 via injection point 239a. In this way, heated product effluent stream 236 flows perpendicularly or substantially perpendicularly to the movement of regenerated catalyst stream 238 in radial flow moving bed reactor 242 as discussed above for heated light hydrocarbon feed stream 112 and regenerated catalyst stream 114.

In some embodiments, regenerated catalyst stream 238 will be heated to a desired temperature to carry the thermal energy necessary for the endothermic reactions of the heated product effluent stream 236 that take place inside the moving catalyst bed 244 as discussed above for regenerated catalyst stream 114.

Radial flow moving bed reactor 242 includes moving catalyst bed 244 formed by flowing a catalyst composition comprising catalyst particles from regenerated catalyst stream 238 through injection points 239a at the upper portion of radial flow moving bed reactor 242 so that the catalyst flows downward through perforated container 243. Heated product effluent stream 236 flows into region 240 via injection point 237a and then through perforated wall 247 to enter and make contact with moving catalyst bed 244. As a result of heated product effluent stream 236 contacting moving catalyst bed 244 in radial flow moving bed reactor 242 under reaction conditions, as discussed above, sufficient to crack the uncracked light hydrocarbons in heated product effluent stream 236, product effluent stream 248 comprises more $C_2$ to $C_{10}$ hydrocarbon product and hydrogen than the product effluent stream 230 from the radial flow moving bed reactor 216 in the series. According to some embodiments, radial flow moving bed reactor 242 has region 246 for receiving product effluent stream 248 from the moving catalyst bed 244, as it exits perforated container 243 through perforated wall 245. The heated product effluent stream 236 thereafter exits radial flow moving bed reactor 242 via exit point 237b as product effluent stream 248, i.e., a $C_2$ to $C_{10}$ hydrocarbon product and hydrogen, that is then sent downstream for further processing. The regenerated catalyst stream 238 exits radial flow moving bed reactor 242 via exit point 239b as spent catalyst stream 250 and is sent to a riser-type catalyst regeneration unit for regeneration as discussed above in reference to FIG. 1.

Multi-stage reactor system 200 is not limited to two radial flow moving bed reactors 216 and 242 as shown in FIG. 3, and more than two reactors may be used (e.g., 3, 4, 5, 6, 7, and 8). The radial flow moving bed reactors can be arranged either in parallel and/or consecutive sequences to obtain better yield. For example, in non-limiting illustrative embodiments, each reactor in the series of radial flow moving bed reactors, other than the first radial flow moving bed reactor in the series, receives a product effluent stream from the prior reactor in the series and processes the product effluent stream from the prior reactor in the series to produce another product effluent stream comprising more $C_2$ to $C_{10}$ hydrocarbon product and hydrogen than the product effluent stream from the prior reactor in the series.

Figure 4:
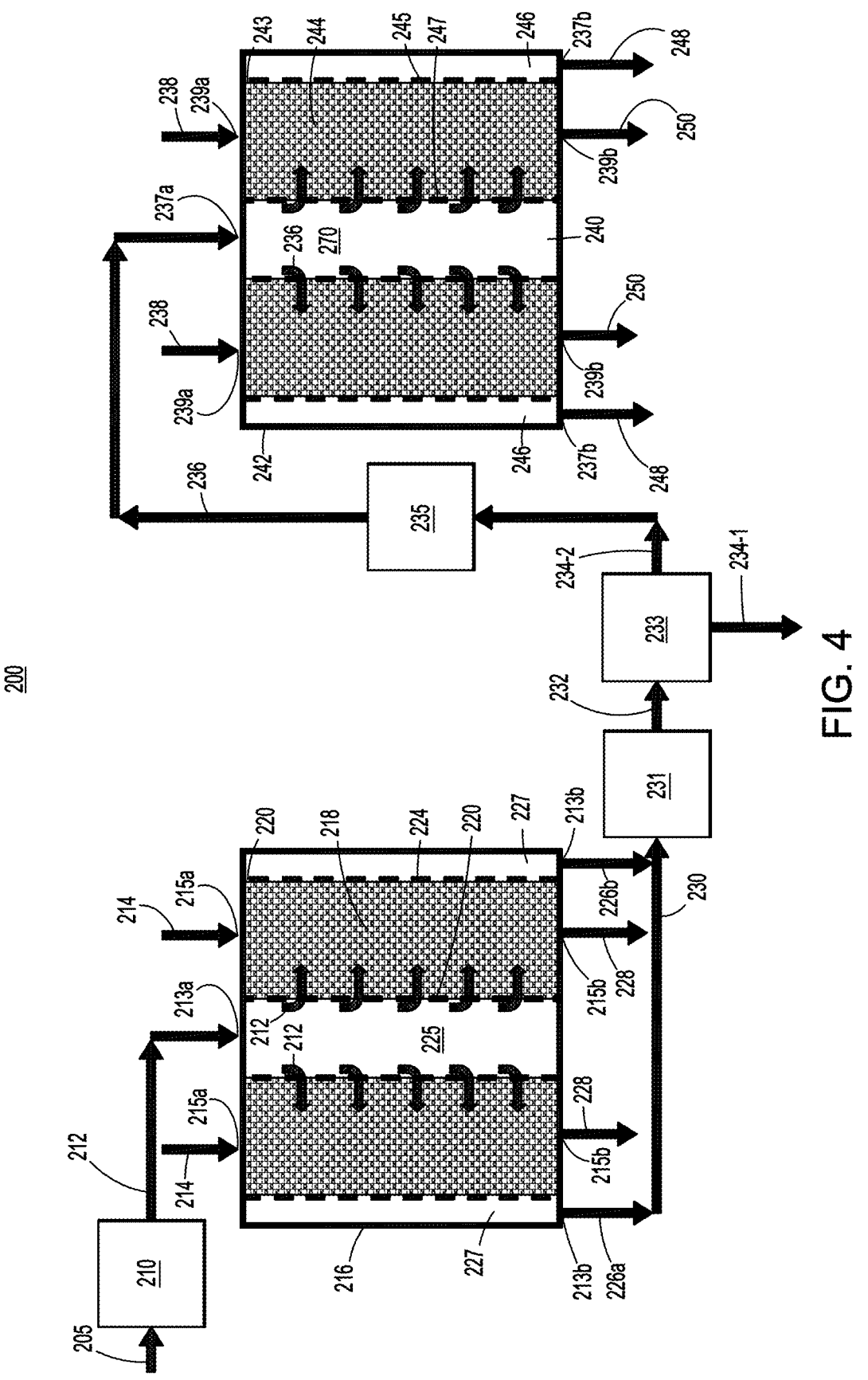
FIG. 4 illustrates a multi-stage reactor system with radial flow moving bed reactors, external heating elements and an inter-stage product separation unit for use in converting a light hydrocarbon feed comprising $C_1$-$C_3$ alkanes to a product effluent stream comprising a $C_2$ to $C_{10}$ hydrocarbon product and hydrogen, according to an illustrative embodiment.

In an alternate embodiment, as shown in FIG. 4, when product effluent stream 230 contains an amount of uncracked light hydrocarbons and an amount of $C_2$ to $C_{10}$ hydrocarbon product and hydrogen, it may be desirable to separate the uncracked light hydrocarbons from the desired $C_2$ to $C_{10}$ hydrocarbon product and hydrogen so that each can be separately processed. In an illustrative embodiment, when the product effluent stream 230 exits radial flow moving bed reactor 216 it can be at a temperature ranging from about 500° C. to about 1200° C. Thus, in order to cool the product effluent stream 230 to a suitable temperature to allow for separating the uncracked light hydrocarbons from the desired $C_2$ to $C_{10}$ hydrocarbon product and hydrogen in separation unit 233, product effluent stream 230 is sent to cooling unit 231. Cooling unit 231 can be, for example, a heat exchanger where product effluent stream 230 is cooled using a stream such as water to transfer the heat from product effluent stream 230 to the water stream thereby producing, for example, steam. The cooled product effluent stream 232 then exits cooling unit 231 at a temperature ranging from about 20° C. to about 60° C.

Cooled product effluent stream 232 can then be sent to separation unit 233 to separate the uncracked light hydrocarbons from the desired $C_2$ to $C_{10}$ hydrocarbon product and hydrogen. For example, the $C_2$ to $C_{10}$ hydrocarbon product and hydrogen can be separated by condensation to separate liquid hydrocarbons from gaseous components. The liquid hydrocarbon can then be removed, and the gaseous components can be sent to the next reactor. The separation unit 233 produces stream 234-1 composed primarily of $C_2$ to $C_{10}$ hydrocarbon product and hydrogen which is sent downstream for further processing, and stream 234-2 composed primarily of uncracked light hydrocarbon which is sent to heating unit 235 and then fed into next reactor for further conversion to desired products.

Alternative embodiments with regard to FIGS. 5A-5C will now be described for a system with a radial flow moving bed reactor with internal heating elements. System 400 of FIGS. 5A-5C may include one or more radial flow moving bed reactors arranged in series or parallel for cracking the light hydrocarbon feed to form a $C_2$ to $C_{10}$ hydrocarbon product and hydrogen. While the exemplary embodiments are described in FIGS. 5A-5C with system 400 having one radial flow moving bed reactor, it is to be appreciated that any number of radial flow moving bed reactors arranged in series or parallel are contemplated herein. For example, illustrative embodiments of present disclosure may have 1, 2, 3, 4, 5, 6, or 7 radial flow moving bed reactors arranged in series or parallel. In addition, FIGS. 5A-5C illustrate radial flow moving bed reactor 416 as an outward flowing radial flow moving bed reactor. However, this is merely exemplary, and radial flow moving bed reactor 416 as an inward flowing radial flow moving bed reactor is also contemplated herein.

FIG. 5A illustrates system 400 including radial flow moving bed reactor 416 containing heating unit 430, in which light hydrocarbon feed stream 405 flows radially through radial flow moving bed reactor 416 via injection point 413a while regenerated catalyst stream 414 moves vertically downward through radial flow moving bed reactor 416 via injection points 415a. In this way, light hydrocarbon feed stream 405 flows perpendicularly or substantially perpendicularly to the movement of regenerated catalyst stream 414 in radial flow moving bed reactor 416.

Radial flow moving bed reactor 416 is similar to radial flow moving bed reactor 116 as discussed above for FIG. 2A, i.e., as an outward flowing radial flow moving bed reactor. This is merely illustrative and other configurations such as inward flowing radial flow moving bed reactors are contemplated herein.

To implement this perpendicular or substantially perpendicular flow, the process may involve allowing particles of regenerated catalyst stream 414 to enter radial flow moving bed reactor 416 at injection points 415a and move slowly by gravity through the radial flow moving bed reactor 416 to the exit points 415b of radial flow moving bed reactor 416. The injection points 415a of the radial flow moving bed reactor 416 are vertically above the exit points 415b of radial flow moving bed reactor 416. The movement, by gravity, of particles of regenerated catalyst stream 414 from the injection points to exit points of radial flow moving bed reactor 416 forms a moving catalyst bed 418 in radial flow moving bed reactor 416.

In some embodiments, regenerated catalyst stream 414 will be heated to a desired temperature to carry the thermal energy necessary for the endothermic reactions of the heated light hydrocarbon feed stream 412 that take place inside the moving catalyst bed 418 as discussed above for regenerated catalyst stream 114.

Radial flow moving bed reactor 416 includes heating unit 430 located in region 425 for heating light hydrocarbon feed stream 405 to generate heated light hydrocarbon feed stream 412 for the endothermic reactions of the heated light hydrocarbon feed stream 412 that take place inside the moving catalyst bed 418. Heating unit 430 can be any suitable heating unit as discussed above for heating unit 110 capable of heating light hydrocarbon feed stream 405 to a desired temperature to carry the thermal energy necessary for the endothermic reactions that take place inside the moving catalyst bed 418.

Radial flow moving bed reactor 416 includes moving catalyst bed 418 which is formed by flowing a catalyst composition comprising catalyst particles from regenerated catalyst stream 414 through injection points 415a at the upper portion of radial flow moving bed reactor 416 so that the catalyst flows downward through perforated container 420. Perforated container 420, according to embodiments of the present disclosure, is adapted so that it keeps the catalyst particles contained within perforated container 420, while allowing heated light hydrocarbon feed stream 412 to be able to flow into perforated container 420 and contact moving catalyst bed 418. Thus, the perforations in perforated walls 422 and 424 may be large enough to have sufficient flow of heated light hydrocarbon feed stream 412 through, but small enough such that the catalyst particles are contained within perforated container 420.

Light hydrocarbon feed stream 405 flows into region 425 via injection point 413a through heating unit 430 where it is heated to the desired temperature. Heated light hydrocarbon feed stream 412 then passes through perforated wall 422 to enter and make contact with moving catalyst bed 418. As a result of heated light hydrocarbon feed stream 412 contacting moving catalyst bed 418 in radial flow moving bed reactor 416 under reaction conditions as discussed above sufficient to crack the light hydrocarbons in heated light hydrocarbon feed stream 412, product effluent stream 426 comprising a $C_2$ to $C_{10}$ hydrocarbon product and hydrogen is formed. According to some embodiments, radial flow moving bed reactor 416 has region 427 for receiving product effluent stream 426 from the moving catalyst bed 418, as it exits perforated container 420 through perforated wall 424. Product effluent stream 426 exits radial flow moving bed reactor 416 via exit points 413b and sent downstream for further processing.

The regenerated catalyst stream 414 exits radial flow moving bed reactor 416 via exit points 415b as spent catalyst stream 428 and is sent to a riser-type catalyst regeneration unit for regeneration as discussed above in reference to FIG. 1.

FIGS. 5B and 5C illustrate alternative embodiments of FIG. 5A. For example, FIG. 5B shows heating unit 430 located in moving catalyst bed 418 as an outward flowing radial flow moving bed reactor. However, this is merely illustrative and other configurations such as heating unit 430 located in moving catalyst bed 418 as an inward flowing radial flow moving bed reactor are contemplated herein. FIG. 5C shows heating unit 430 located in region 427 of radial flow moving bed reactor 416 as an inward flowing radial flow moving bed reactor.

In one or more additional illustrative embodiments, as may be combined with the preceding paragraphs, FIG. 6 illustrates multi-stage reactor system 500 including radial flow moving bed reactors 516 and 542 with respective heating units 503 and 560. Radial flow moving bed reactors 516 and 542 are similar to radial flow moving bed reactor 116 as discussed above for FIG. 2A, i.e., as an outward flowing radial flow moving bed reactor. However, the multi-stage reactor system 500 of the present disclosure is not limited to such a configuration and any combination of outward and inward flowing radial flow moving bed reactors are contemplated. In addition, the multi-stage reactor system 500 is not limited to two radial flow moving bed reactors as shown in FIG. 5, and more than two reactors may be used (e.g., 3, 4, 5, 6, 7, and 8). The radial flow moving bed reactors can be arranged either in parallel and/or consecutive sequences to obtain better yield. Further, the multi-stage reactor system 500 is not limited to heating units 503 and 560 located in respective regions 525 and 540, and any number of configurations are contemplated herein based in part, for example, on FIGS. 5A-5C.

Multi-stage reactor system 500 includes radial flow moving bed reactor 516 containing heating unit 503. Multi-stage reactor system 500 includes radial flow moving bed reactor 516, in which light hydrocarbon feed stream 505 flows radially through radial flow moving bed reactor 516 via injection point 513a while regenerated catalyst stream 514 moves vertically downward through radial flow moving bed reactor 516 via injection point 515a. In this way, light hydrocarbon feed stream 505 flows perpendicularly or substantially perpendicularly to the movement of regenerated catalyst stream 514 in radial flow moving bed reactor 516.

To implement this perpendicular or substantially perpendicular flow, the process may involve allowing particles of regenerated catalyst stream 514 to enter radial flow moving bed reactor 516 at injection points 515a and move slowly by gravity through the radial flow moving bed reactor 516 to the exit points 515b of radial flow moving bed reactor 516. The injection points 515a of the radial flow moving bed reactor 516 are vertically above the exit points 515b of radial flow moving bed reactor 516. The movement, by gravity, of particles of regenerated catalyst stream 514 from the injection points 515a to exit points 515b of radial flow moving bed reactor 516 forms a moving catalyst bed 518 in radial flow moving bed reactor 516.

In some embodiments, regenerated catalyst stream 514 will be heated to a desired temperature to carry the thermal energy necessary for the endothermic reactions of the heated light hydrocarbon feed stream 512 that take place inside the moving catalyst bed 518 as discussed above for regenerated catalyst stream 114.

Radial flow moving bed reactor 516 includes heating unit 503 located in region 525 for heating light hydrocarbon feed stream 505 to generate heated light hydrocarbon feed stream 512 for the endothermic reactions of the heated light hydrocarbon feed stream 512 that take place inside the moving catalyst bed 518. Heating unit 503 can be any suitable heating unit as discussed above for heating unit 110 capable of heating light hydrocarbon feed 505 to a desired temperature to carry the thermal energy necessary for the endothermic reactions that take place inside the moving catalyst bed 518.

Radial flow moving bed reactor 516 further includes moving catalyst bed 518 which is formed by flowing a catalyst composition comprising catalyst particles from regenerated catalyst stream 514 through injection points 515a at the upper portion of radial flow moving bed reactor 516 so that the catalyst flows downward through perforated container 520. Light hydrocarbon feed stream 505 flows into region 525 via injection point 513a through heating unit 503 where it is heated to the desired temperature. Heated light hydrocarbon feed stream 512 then passes through perforated wall 522 to enter and make contact with moving catalyst bed 518. As a result of heated light hydrocarbon feed stream 512 contacting moving catalyst bed 518 in radial flow moving bed reactor 516 under reaction conditions as discussed above sufficient to crack the light hydrocarbons in heated light hydrocarbon feed stream 512, product effluent streams 526a and 526b each comprising a $C_2$ to $C_{10}$ hydrocarbon product and hydrogen is formed. According to some embodiments, radial flow moving bed reactor 516 has region 527 for receiving product effluent streams 526a and 526b from the moving catalyst bed 518, as it exits perforated container 520 through perforated wall 524.

The regenerated catalyst stream 514 exits radial flow moving bed reactor 516 via exit point 515b as spent catalyst stream 528 and is sent to a riser-type catalyst regeneration unit for regeneration as discussed above in reference to FIG. 1.

Following cracking of the heated light hydrocarbon feed stream 512, the product effluent streams 526a and 526b can contain an amount of uncracked heated light hydrocarbon feed stream 512. Accordingly, in one embodiment, product effluent streams 526a and 526b exit radial flow moving bed reactor 516 via exit points 513b where they are combined as product effluent stream 530 and sent to radial flow moving bed reactor 542 containing heating unit 560 in region 540. Heating unit 560 can be any suitable heating unit capable of heating product effluent streams 526a and 526b to a desired temperature to carry the thermal energy necessary for the endothermic reactions that take place inside the moving catalyst bed 544 as discussed above.

In some embodiments, regenerated catalyst stream 538 will be heated to a desired temperature to carry the thermal energy necessary for the endothermic reactions of the heated product effluent stream 541 that take place inside the moving catalyst bed 544 as discussed above for regenerated catalyst stream 114.

Radial flow moving bed reactor 542 includes moving catalyst bed 544 which is formed by flowing a catalyst composition comprising catalyst particles from regenerated catalyst stream 538 through injection points 539a at the upper portion of radial flow moving bed reactor 542 so that the catalyst flows downward through perforated container 543. Product effluent stream 530 flows into region 540 via injection point 537a through heating unit 560 where it is heated to the desired temperature as discussed above. Heated product effluent stream 541 then passes through perforated wall 547 to enter and make contact with moving catalyst bed 544 to form product effluent stream 548 comprising a $C_2$ to $C_{10}$ hydrocarbon product and hydrogen. According to some embodiments, radial flow moving bed reactor 542 has region 570 for receiving product effluent stream 548 from the moving catalyst bed 544, as it exits perforated container 543 through perforated wall 545. Product effluent stream 548 then exits radial flow moving bed reactor 542 through exit points 537b and is sent downstream for further processing.

The regenerated catalyst stream 538 exits radial flow moving bed reactor 542 via exit points 539B as spent catalyst stream 550 and is sent to a riser-type catalyst regeneration unit for regeneration as discussed above in reference to FIG. 1.

In an alternate embodiment, as shown in FIG. 7, when product effluent stream 530 contains an amount of uncracked light hydrocarbons and an amount of $C_2$ to $C_{10}$ hydrocarbon product and hydrogen, it may be desirable to separate the uncracked light hydrocarbons from the desired $C_2$ to $C_{10}$ hydrocarbon product and hydrogen so that each can be separately processed. In an illustrative embodiment, when the product effluent stream 530 exits radial flow moving bed reactor 516 it can be at a temperature ranging from about 500° C. to about 1200° C. Thus, in order to cool the product effluent stream 530 to a suitable temperature to allow for separating the uncracked light hydrocarbons from the desired $C_2$ to $C_{10}$ hydrocarbon product and hydrogen in separation unit 533, product effluent stream 530 is sent to cooling unit 531. Cooling unit 531 can be, for example, a heat exchanger where product effluent stream 530 is cooled using a stream such as water to transfer the heat from product effluent stream 530 to the water stream thereby producing, for example, steam. The cooled product effluent stream 532 then exits cooling unit 531 at a temperature ranging from about 20° C. to about 60° C.

Cooled product effluent stream 532 can then be sent to separation unit 533 to separate the uncracked light hydrocarbons from the desired $C_2$ to $C_{10}$ hydrocarbon product and hydrogen. For example, the $C_2$ to $C_{10}$ hydrocarbon product and hydrogen can be separated by condensation to separate liquid hydrocarbons from gaseous components. The liquid hydrocarbon can then be removed, and the gaseous components can be sent to the next reactor. The separation unit 533 produces stream 534-1 composed primarily of $C_2$ to $C_{10}$ hydrocarbon product and hydrogen which is sent downstream for further processing, and stream 534-2 composed primarily of uncracked light hydrocarbon which is sent to radial flow moving bed reactor 542 where it is heated utilizing heating unit 560 and further converted into desired products.

According to an aspect of the present disclosure, a process comprises:

flowing a catalyst composition comprising catalyst particles into a radial flow moving bed reactor, wherein the catalyst particles move by gravity through the radial flow moving bed reactor to an exit point of the radial flow moving bed reactor, wherein the catalyst particles form a moving catalyst bed in the radial flow moving bed reactor, flowing a light hydrocarbon feed stream comprising $C_1$ to $C_3$ alkanes into the radial flow moving bed reactor in a manner so that the light hydrocarbon feed stream flows radially inward or radially outward through the moving catalyst bed and thereby contacts the catalyst particles under reaction conditions to produce a product effluent stream comprising a $C_2$ to $C_{10}$ hydrocarbon product and hydrogen, and flowing the product effluent stream from the radial flow moving bed reactor.

In one or more additional illustrative embodiments, as may be combined with the preceding paragraphs, the process further comprises flowing the light hydrocarbon feed stream to a heating unit located outside the radial flow moving bed reactor to generate a heated light hydrocarbon feed stream and flowing the heated light hydrocarbon feed stream into the radial flow moving bed reactor.

In one or more additional illustrative embodiments, as may be combined with the preceding paragraphs, the heated light hydrocarbon feed stream is at a temperature of about 500° C. to about 1200° C.

In one or more additional illustrative embodiments, as may be combined with the preceding paragraphs, flowing the light hydrocarbon feed stream into the radial flow moving bed reactor takes place adiabatically.

In one or more additional illustrative embodiments, as may be combined with the preceding paragraphs, flowing the light hydrocarbon feed stream radially inward or radially outward causes the flow of the light hydrocarbon feed stream to be perpendicular or substantially perpendicular to movement of the moving catalyst bed.

In one or more additional illustrative embodiments, as may be combined with the preceding paragraphs, flowing the light hydrocarbon feed stream into the radial flow moving bed reactor comprises flowing the light hydrocarbon feed stream through one or more heating units located within the radial flow moving bed reactor in a manner so that a heated light hydrocarbon feed stream flows radially inward or radially outward through the moving catalyst bed and thereby contacts the catalyst particles under reaction conditions to produce the product effluent stream.

In one or more additional illustrative embodiments, as may be combined with the preceding paragraphs, the heated light hydrocarbon feed stream is at a temperature of about 500° C. to about 1200° C.

In one or more additional illustrative embodiments, as may be combined with the preceding paragraphs, a pressure drop across the radial flow moving bed reactor is from about 1 psi to about 10 psi.

In one or more additional illustrative embodiments, as may be combined with the preceding paragraphs, the process further comprises:

flowing spent catalyst from a bottom of the radial flow moving bed reactor to a catalyst regeneration unit, regenerating the spent catalyst in the catalyst regeneration unit, and flowing the regenerated catalyst from the catalyst regeneration unit to a top of the radial flow moving bed reactor via a riser.

In one or more additional illustrative embodiments, as may be combined with the preceding paragraphs, the light hydrocarbon feed stream is a natural gas stream.

According to an aspect of the present disclosure, a process comprises:

processing a light hydrocarbon feed stream comprising $C_1$ to $C_3$ alkanes in a series of radial flow moving bed reactors, wherein processing in a first radial flow moving bed reactor in the series of radial flow moving bed reactors comprises:

flowing a first catalyst composition comprising catalyst particles into a first radial flow moving bed reactor, wherein the catalyst particles move by gravity through the first radial flow moving bed reactor to an exit point of the first radial flow moving bed reactor, wherein the catalyst particles form a moving catalyst bed in the first radial flow moving bed reactor, flowing the light hydrocarbon feed stream comprising $C_1$ to $C_3$ alkanes into the first radial flow moving bed reactor in a manner so that the light hydrocarbon feed stream flows radially inward or radially outward through the moving catalyst bed and thereby contacts the catalyst particles under reaction conditions to produce a product effluent stream comprising a $C_2$ to $C_{10}$ hydrocarbon product, hydrogen and unreacted $C_1$ to $C_3$ alkanes, flowing the product effluent stream into a second radial flow moving bed reactor for further processing, flowing spent catalyst from the series of radial flow moving bed reactors to a catalyst regeneration unit, regenerating the spent catalyst in the catalyst regeneration unit, and flowing the regenerated catalyst from the catalyst regeneration unit to the series of radial flow moving bed reactors.

In one or more additional illustrative embodiments, as may be combined with the preceding paragraphs, the process further comprises:

flowing the light hydrocarbon feed stream to a first heating unit located outside the first radial flow moving bed reactor to generate a heated light hydrocarbon feed stream and flowing the heated light hydrocarbon feed stream into the first radial flow moving bed reactor.

In one or more additional illustrative embodiments, as may be combined with the preceding paragraphs, the process further comprises:

flowing the product effluent stream to a second heating unit located outside the second radial flow moving bed reactor to generate a heated product effluent stream and flowing the heated product effluent stream into the second radial flow moving bed reactor.

In one or more additional illustrative embodiments, as may be combined with the preceding paragraphs, the catalyst regeneration unit receives the spent catalyst from a bottom of each of the series of radial flow moving bed reactors and is operatively connected to a riser, and wherein flowing the regenerated catalyst from the catalyst regeneration unit to the series of radial flow moving bed reactors comprises flowing the regenerated catalyst from the riser to a top of each of the series of radial flow moving bed reactors.

In one or more additional illustrative embodiments, as may be combined with the preceding paragraphs, flowing the light hydrocarbon feed stream into the first radial flow moving bed reactor and flowing the product effluent stream into the second radial flow moving bed reactor each takes place adiabatically.

In one or more additional illustrative embodiments, as may be combined with the preceding paragraphs, flowing the light hydrocarbon feed stream into the first radial flow moving bed reactor comprises flowing the light hydrocarbon feed stream through one or more heating units located within the first radial flow moving bed reactor in a manner so that a heated light hydrocarbon feed stream flows radially inward or radially outward through the moving catalyst bed and thereby contacts the catalyst particles under reaction conditions to produce the product effluent stream.

In one or more additional illustrative embodiments, as may be combined with the preceding paragraphs, where each reactor in the series of radial flow moving bed reactors, other than the first radial flow moving bed reactor in the series, receives a product effluent stream from the prior reactor in the series and processes the product effluent stream from the prior reactor in the series to produce another product effluent stream comprising more $C_2$ to $C_{10}$ hydrocarbon product and hydrogen than the product effluent stream from the prior reactor in the series.

In one or more additional illustrative embodiments, as may be combined with the preceding paragraphs, a pressure drop across each reactor in the series of radial flow moving bed reactors is from about 1 psi to about 10 psi.

In one or more additional illustrative embodiments, as may be combined with the preceding paragraphs, the light hydrocarbon feed stream is a natural gas stream.

In one or more additional illustrative embodiments, as may be combined with the preceding paragraphs, flowing the light hydrocarbon feed stream and the product effluent stream radially inward or radially outward causes the flow of the light hydrocarbon feed stream and the product effluent stream to be perpendicular or substantially perpendicular to movement of the moving catalyst bed.

Various features disclosed herein are, for brevity, described in the context of a single embodiment, but may also be provided separately or in any suitable sub-combination. All combinations of the embodiments are specifically embraced by the illustrative embodiments disclosed herein just as if each and every combination was individually and explicitly disclosed. In addition, all sub-combinations listed in the embodiments describing such variables are also specifically embraced by the present disclosure and are disclosed herein just as if each and every such sub-combination was individually and explicitly disclosed herein.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A process, comprising:

processing a light hydrocarbon feed stream comprising $C_1$ to $C_3$ alkanes in a series of radial flow moving bed reactors, wherein processing in a first radial flow moving bed reactor in the series of radial flow moving bed reactors comprises:

flowing a first catalyst composition comprising catalyst particles into the first radial flow moving bed reactor, wherein the catalyst particles move by gravity through the first radial flow moving bed reactor to an exit point of the first radial flow moving bed reactor, wherein the catalyst particles form a moving catalyst bed in the first radial flow moving bed reactor;

flowing the light hydrocarbon feed stream comprising $C_1$ to $C_3$ alkanes into the first radial flow moving bed reactor in a manner so that the light hydrocarbon feed stream flows radially inward or radially outward through the moving catalyst bed and thereby contacts the catalyst particles under reaction conditions to produce a heated first product effluent comprising a $C_2$ to $C_{10}$ hydrocarbon product, hydrogen and unreacted $C_1$ to $C_3$ alkanes;

flowing the heated first product effluent comprising the $C_2$ to $C_{10}$ hydrocarbon product, hydrogen and the unreacted $C_1$ to $C_3$ alkanes to a heat exchanger to produce a cooled first product effluent comprising the $C_2$ to $C_{10}$ hydrocarbon product, hydrogen and the unreacted $C_1$ to $C_3$ alkanes;

flowing the cooled first product effluent into a separation unit to separate the $C_2$ to $C_{10}$ hydrocarbon product and hydrogen from the unreacted $C_1$ to $C_3$ alkanes by condensation to produce a liquid stream comprising the $C_2$ to $C_{10}$ hydrocarbon product and hydrogen and a gaseous stream comprising the unreacted $C_1$ to $C_3$ alkanes;

flowing the gaseous stream comprising the unreacted $C_1$ to $C_3$ alkanes into a second radial flow moving bed reactor to produce a second product effluent comprising a $C_2$ to $C_{10}$ hydrocarbon product and hydrogen;

flowing spent catalyst from the series of radial flow moving bed reactors to a catalyst regeneration unit;

regenerating the spent catalyst in the catalyst regeneration unit; and flowing the regenerated catalyst upwards via a riser from the catalyst regeneration unit to a top of each of the series of radial flow moving bed reactors.

2. The process according to claim 1, further comprising:

flowing the light hydrocarbon feed stream to a first heating unit located outside the first radial flow moving bed reactor to generate a heated light hydrocarbon feed stream; and flowing the heated light hydrocarbon feed stream into the first radial flow moving bed reactor.

3. The process according to claim 2, further comprising:

flowing the gaseous stream comprising the unreacted $C_1$ to $C_3$ alkanes to a second heating unit located outside the second radial flow moving bed reactor to generate a heated gaseous stream comprising the unreacted $C_1$ to $C_3$ alkanes; and flowing the heated gaseous stream comprising the unreacted $C_1$ to $C_3$ alkanes into the second radial flow moving bed reactor.

4. The process according to claim 1, wherein flowing the light hydrocarbon feed stream into the first radial flow moving bed reactor and flowing the gaseous stream comprising the unreacted $C_1$ to $C_3$ alkanes into the second radial flow moving bed reactor each takes place adiabatically.

5. The process according to claim 1, wherein flowing the light hydrocarbon feed stream into the first radial flow moving bed reactor comprises flowing the light hydrocarbon feed stream through one or more heating units located within the first radial flow moving bed reactor in a manner so that a heated light hydrocarbon feed stream flows radially inward or radially outward through the moving catalyst bed and thereby contacts the catalyst particles under reaction conditions to produce the heated first product effluent stream.

6. The process according to claim 1, wherein a pressure drop across each radial flow moving bed reactor in the series of radial flow moving bed reactors is from about 1 psi to about 10 psi.

7. The process according to claim 1, wherein the light hydrocarbon feed stream is a natural gas stream.

8. The process according to claim 1, wherein flowing the light hydrocarbon feed stream radially inward or radially outward causes the flow of the light hydrocarbon feed stream to be perpendicular or substantially perpendicular to movement of the moving catalyst bed.

9. The process according to claim 1, wherein the heated first product effluent is at a temperature of about 500° C. to about 1200° C., and the cooled first product effluent is at a temperature of about 20° C. to about 60° C.

10. The process according to claim 9, wherein the heat exchanger is a cooling unit configured to pass a water stream to transfer heat from the heated first product effluent to the water stream thereby producing the cooled first product effluent as steam.

* * * * *